(12) United States Patent
Bilton

(10) Patent No.: US 10,737,035 B2
(45) Date of Patent: Aug. 11, 2020

(54) PISTON ROD FOR A DRUG DELIVERY DEVICE AND DRUG DELIVERY DEVICE COMPRISING A PISTON ROD

(71) Applicant: Sanofi, Paris (FR)

(72) Inventor: Simon Lewis Bilton, Warwickshire (GB)

(73) Assignee: Sanofi, Paris (FR)

( * ) Notice: Subject to any disclaimer, the term of this patent is extended or adjusted under 35 U.S.C. 154(b) by 641 days.

(21) Appl. No.: 14/915,952

(22) PCT Filed: Sep. 3, 2014

(86) PCT No.: PCT/EP2014/068652
§ 371 (c)(1),
(2) Date: Mar. 2, 2016

(87) PCT Pub. No.: WO2015/032779
PCT Pub. Date: Mar. 12, 2015

(65) Prior Publication Data
US 2016/0199587 A1    Jul. 14, 2016

(30) Foreign Application Priority Data
Sep. 3, 2013 (EP) .................................. 13182758

(51) Int. Cl.
*A61M 5/315* (2006.01)
*A61M 5/20* (2006.01)

(52) U.S. Cl.
CPC .......... *A61M 5/31553* (2013.01); *A61M 5/20* (2013.01); *A61M 5/31541* (2013.01);
(Continued)

(58) Field of Classification Search
CPC ................ A61M 5/31553; A61M 5/20; A61M 5/31541; A61M 5/31583; A61M 5/31585; A61M 5/31551
(Continued)

(56) References Cited

U.S. PATENT DOCUMENTS 2,423,762 A * 7/1947 Everett ................. A61M 5/347
604/241
2009/0275916 A1* 11/2009 Harms .................... A61M 5/24
604/506
(Continued)

FOREIGN PATENT DOCUMENTS

CN      102083489      6/2011
JP      2011-519600    7/2011
(Continued)

OTHER PUBLICATIONS

International Search Report and Written Opinion in International Application No. PCT/EP2014/068652, dated Oct. 13, 2014, 12 pages.
(Continued)

Primary Examiner — Brandy S Lee
Assistant Examiner — Hong-Van N Trinh
(74) Attorney, Agent, or Firm — Fish & Richardson P.C.

(57) ABSTRACT

A piston rod for a drug delivery device includes a first thread with a first inner diameter and a second thread with a second inner diameter. The first inner diameter of the first thread is smaller than the second inner diameter of the second thread. The first thread includes a first pitch and the second thread includes a second pitch. The first and the second pitch have the same magnitude.

18 Claims, 19 Drawing Sheets

(52) U.S. Cl.
CPC ... *A61M 5/31583* (2013.01); *A61M 2205/581* (2013.01); *A61M 2205/586* (2013.01)

(58) Field of Classification Search
USPC .......................................................... 604/211
See application file for complete search history.

(56) References Cited

U.S. PATENT DOCUMENTS

| | | | | |
|---|---|---|---|---|
| 2009/0326459 | A1* | 12/2009 | Shipway | A61M 5/31511 604/155 |
| 2010/0016806 | A1* | 1/2010 | Glejbol | A61M 5/31551 604/211 |
| 2010/0114025 | A1* | 5/2010 | Moller | A61M 5/31565 604/135 |
| 2012/0157932 | A1 | 6/2012 | Glejbol et al. | |
| 2012/0283659 | A1* | 11/2012 | Kouyoumjian | A61M 5/31551 604/211 |
| 2013/0310761 | A1* | 11/2013 | Plumptre | A61M 5/31585 604/211 |

FOREIGN PATENT DOCUMENTS

| | | |
|---|---|---|
| JP | 2012-528628 | 11/2012 |
| WO | WO2009/132778 | 11/2009 |
| WO | WO2010/139640 | 12/2010 |
| WO | WO 2012/140097 | 10/2012 |
| WO | WO2013/010884 | 1/2013 |

OTHER PUBLICATIONS

International Preliminary Report on Patentability in International Application No. PCT/EP2014/068652, dated Mar. 8, 2016, 10 pages.

Rote Liste, "50. Hypophysen-, Hypothalamushormone, andere regulatorische Peptide u. ihre Hemmstoffe," Chapter 50, ed. 2008, 20 pages.

* cited by examiner

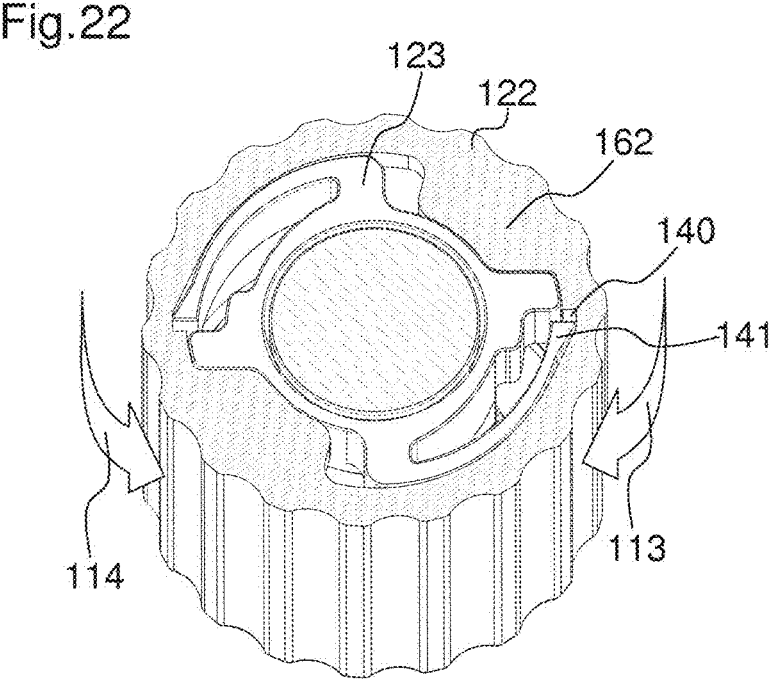

PISTON ROD FOR A DRUG DELIVERY DEVICE AND DRUG DELIVERY DEVICE COMPRISING A PISTON ROD

CROSS-REFERENCE TO RELATED APPLICATIONS

This application is a U.S. national stage application under 35 USC § 371 of International Application No. PCT/EP2014/068652, filed on Sep. 3, 2014, which claims priority to European Patent Application No. 13182758.6, filed on Sep. 3, 2013, the entire contents of which are incorporated herein by reference.

TECHNICAL FIELD

The present disclosure relates to a piston rod for a drug delivery device and a drug delivery device comprising a piston rod. In some aspects of the present invention, a piston rod for a drug delivery device has improved properties.

SUMMARY

According to one aspect of the disclosure, a piston rod for a drug delivery device is provided, the piston rod comprising a first thread with a first inner diameter and a second thread with a second inner diameter, wherein the first inner diameter is different from the second inner diameter. In particular, the first inner diameter is smaller than the second inner diameter. Furthermore, the first thread of the piston rod comprises a first pitch and the second thread comprises a second pitch wherein the first and the second pitch have the same magnitude. The piston rod may be configured to be moved towards a distal end of the device in order to dispense a dose of medication.

The term "distal end" may describe an end of the device or a part thereof which is closest to a dispensing end of the device. The term "proximal end" may describe an end of the device or a part thereof which is furthest away from the dispensing end of the device. Analogously, the term "distal direction" may describe a direction towards a dispensing end of the device and the term "proximal direction" may describe a direction away from the dispensing end of the device.

In particular, the piston rod may be configured as a lead screw. The piston rod may be configured to act on a bung or a piston in a medication container, for example a cartridge, causing a medication to be dispensed from the container. A bearing surface may be arranged at a distal end of the piston rod, wherein the bearing surface is configured to abut the bung or piston. The threads of the piston rod may be configured to engage with further members of the drug delivery device, for example members which are configured to drive the piston rod towards a dispensing end of the device during the dispensing of a dose, or members which inhibit a movement of the piston rod during the setting of a dose.

The drug delivery device may be an injection device. The drug delivery device may be a variable dose device such that a user can select the size of a dose. The drug delivery device may be configured for multiple dose applications. The medication may be delivered to a user by means of a needle. The drug delivery device may be a pen-type device. The drug delivery device may be disposable. The term "disposable" means that the drug delivery device cannot be reused after an available amount of medication has been delivered from the drug delivery device. The drug delivery device may be configured to deliver a liquid medication. The medication may be, for example, insulin.

An advantage of the piston rod having a first thread with an inner diameter which is smaller than the inner diameter of a second thread may be that a friction force between a member which is engaged with the first thread of the piston rod and the piston rod may be kept small. Thereby, a torque which is required to screw the member along the piston rod may be kept small. Due to the second thread having an inner diameter which is larger than the inner diameter of the first thread, the piston rod may have a sufficient mechanical stability. Furthermore, the contact surface between the piston rod and a member engaged with the second thread may be large enough to provide a sufficient dosing accuracy.

An advantage of a piston rod wherein the first thread comprises a first pitch and the second thread comprises a second pitch, wherein the first and the second pitch have the same magnitude, is that the number of rotations around the piston rod of a first member may be equal to the number of rotations around the piston rod of a second member, when both members are screwed along the piston rod the same axial distance. The first member may be for example a member which is screwed along the piston rod during a dose dispense operation. The second member may be for example a member which is screwed along the piston rod during a dose set operation. In an alternative embodiment, the first and the second pitch may have a different magnitude.

According to one embodiment, at least one of the first and the second thread extends over the whole length of the piston rod. Preferably, both of the first and the second thread extend over the whole length of the piston rod. Alternatively, one of the first and the second thread extend over the whole length of the piston rod, while the other one of the first and the second thread extends only in a section of the piston rod, for example in a proximal section or in a distal section of the piston rod. A distal section may be a section which is directed towards a dispensing end of the drug delivery device. A proximal section may be a section which is faced away from the dispensing end of the drug delivery device. Alternatively, both the first and the second thread may extend only in a section of the piston rod. In one embodiment, these sections may overlap. In an alternative embodiment, these sections may not overlap. In particular, theses sections may be arranged with a distance to each other.

According to one embodiment, the first and the second threads are counter-handed. The first thread may be left-handed and the second thread may be right-handed or vice versa. According to one embodiment, the first and the second threads intersect each other. In particular, the first and the second threads run crosswise.

According to one embodiment, at least one of the first and the second thread is a twin-start thread. A twin-start thread comprises two thread starts. Thereby, a member, for example a piston rod nut or a locking member, being engaged with the twin-start thread may be mounted with increased stability. Furthermore, the piston rod may be guided with increased stability. Preferably, both the first and the second threads are twin-start threads.

According to one embodiment, the piston rod may comprise at least one axial groove or at least one axial spline. For example, the piston rod may comprise two axial grooves or two axial splines. The grooves or splines may be arranged at opposing sides of the piston rod. The at least one axial groove or at least one axial spline may be configured to rotationally fix the piston rod with respect to a housing of the drug delivery device. This may be achieved by the at least one groove or spline engaging with a corresponding spline or groove of a member which is rotationally fixed with respect to the housing. Alternatively, the at least one groove or spline may engage with a corresponding spline or groove of the housing. Thereby, the piston rod may be rotationally fixed with respect to the housing during the setting and dispensing of a dose.

According to a further aspect of the invention, a drug delivery device is provided, the drug delivery device comprising a piston rod. The piston rod may be configured as described above. Furthermore, the drug delivery device comprises a housing. The piston rod may be rotationally fixed to the housing, in particular both during the setting and dispensing of a dose.

The drug delivery device may comprise further members which may be engaged with the piston rod. For example, the drug delivery device may comprise a member which is rotated about the piston rod during the setting of a dose. The member may be engaged with the second thread. Furthermore, the drug delivery device may comprise a member which is rotated about the piston rod during the dispense of a dose. The member may be engaged with the first thread.

According to one embodiment, the drug delivery device comprises a locking member which is engaged with the first thread of the piston rod, wherein a movement of the piston rod is inhibited when the locking member is in a locking state. The locking member may be axially fixed with respect to the housing. For example, the locking member may comprise a flange which abuts a member of the drug delivery device or the housing. In a locking state, the locking member may be rotationally fixed with respect to the housing of the drug delivery devise. The locking member may be in a locking state due to the engagement with a further member of the drug delivery device during the setting of a dose. Thereby, an axial movement of the piston rod may be inhibited. During the dispense of a dose, the locking member may be released from its locking state. As an example, the engagement with the further member of the drug delivery device may be released. In particular, the locking member may be free to rotate with respect to the housing when it is released from the locking state. Thereby, the piston rod may be enabled to axially move towards a dispensing end of the device. Thereby, the dispense of a dose of medication may be achieved. The locking member may be, for example, a lock nut.

According to one embodiment, the locking member is configured to overhaul the piston rod during the dispense of a dose. In particular, the locking member may be axially secured with respect to the housing, but may rotate when the piston rod is moved in a direction towards a dispensing end of the device. Thereby, the locking member may be rotated about the piston rod, in particular overhaul the piston rod. Since the locking member is engaged with the first thread of the piston rod, which has a smaller inner diameter than the second thread of the piston rod, the overhauling torque may be kept small.

According to a further embodiment, the drug delivery device comprises a piston rod nut being engaged with the second thread of the piston rod, and being configured to rotate along the piston rod in a direction towards a proximal end of the device in order to set a dose of medication. In particular, the piston rod nut may be rotated towards a proximal end of the device when a dose setting member is rotated in a dose setting direction.

According to a further embodiment, the drive assembly comprises a rotation member, wherein the piston rod nut is rotated by a rotation of the rotation member. In particular, the piston rod nut may be engaged with the rotation member.

The rotation member may be a sleeve. The piston rod nut may be rotationally fixed, but axially moveable with respect to the rotation member. The rotation member may be rotated in order to set a dose. When the rotation member is rotated in dose setting direction, the piston rod nut is moved towards a proximal end of the device. When the rotation member is rotated in a dose cancelling direction, the piston rod nut is moved towards a distal end of the device.

According to a further embodiment, the drug delivery device comprises a spring member, causing the piston rod to move in a direction towards the distal end of the device by exerting a force on the piston rod nut. The spring member may be, for example, a coil spring. The spring member may be compressed during the setting of a dose.

In particular, an overhauling torque which causes the locking member to rotate may be caused by the spring member exerting a force on the piston rod nut. In particular, the overhauling torque causes the locking member to rotate when the locking member is not in its locking state, in particular when the actuator is activated. Thereby, the locking member may be screwed along the piston rod, in particular overhaul the piston rod.

When the piston rod nut is rotated towards the proximal end of the device by a rotation of the dose setting member, the piston rod nut may compress the spring member. Thereby, energy may be stored in the spring member, which may be released during the dispense of a dose. The piston rod nut may be rotated towards a dispensing end of the device when the dose setting member is rotated in a dose cancelling direction. During the dispense of a dose, the piston rod nut may drive the piston rod towards a distal end of the device. In particular, the spring member may exert a force on the piston rod nut and drive the piston rod nut, and thereby drive the piston rod towards a distal end of the device.

A relative rotational movement between the piston rod nut and the piston rod may be prevented during the dispense of a dose. This may be achieved by the piston rod nut being rotationally fixed with respect to the housing, and the piston rod being rotationally fixed with respect to the housing. When the piston rod nut is moved towards the dispensing end of the device in order to deliver a dose of medication, the piston rod is moved towards the dispensing end together with the piston rod nut.

According to a further embodiment, the drug delivery device comprises an actuator, wherein the locking member is moved out of its locking position when the actuator is activated. The actuator may be a trigger. The actuator may be configured to be operated by a user in order to dispense a dose of medication. When the actuator is operated it may be axially moved with respect to the housing, for example in a direction towards a dispensing end of the device. When the locking member is in its locking state, the locking member may be engaged with the actuator. When the actuator is activated, the engagement between the actuator and the locking member may be released. Thereby, the locking member may be released from its locking state. Thereby, the locking member may be free to rotate. Preferably, the actuator is rotationally fixed with respect to the housing.

According to a further embodiment, the actuator is in engagement with the at least one axial groove or spline of the piston rod. Thereby, a rotation of the piston rod relative to the housing may be inhibited during dose setting and dose dispensing.

According to another aspect the invention relates to a drug delivery device comprising a piston rod, the piston rod comprising a first thread with a first inner diameter and a second thread with a second inner diameter, wherein the first inner diameter is smaller than the second inner diameter, wherein the first thread comprises a first pitch and the second thread comprises a second pitch, and wherein the first and the second pitch have the same magnitude. The drug delivery device further comprises a locking member being engaged with the first thread of the piston rod, wherein a movement of the piston rod is inhibited when the locking member is in a locking state, and wherein the locking member is configured to overhaul the piston rod during a dispense of a dose.

According to yet another aspect the invention relates to a drug delivery device comprising a piston rod, the piston rod comprising a first thread with a first inner diameter and a second thread with a second inner diameter, wherein the first inner diameter is smaller than the second inner diameter, wherein the first thread comprises a first pitch and the second thread comprises a second pitch, and wherein the first and the second pitch have the same magnitude. The drug delivery device further comprises a locking member being engaged with the first thread of the piston rod, wherein a movement of the piston rod is inhibited when the locking member is in a locking state. The drug delivery device further comprises an actuator, wherein the locking member is released from its locking state when the actuator is activated.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

BRIEF DESCRIPTION OF THE DRAWINGS

FIG. 22 shows an alternative embodiment of the engagement of the rotation member with the dose setting member, FIGS. 23A to 23D explain the operation of the mechanism, as the actuator is activated.

DETAILED DESCRIPTION

Figure 1:
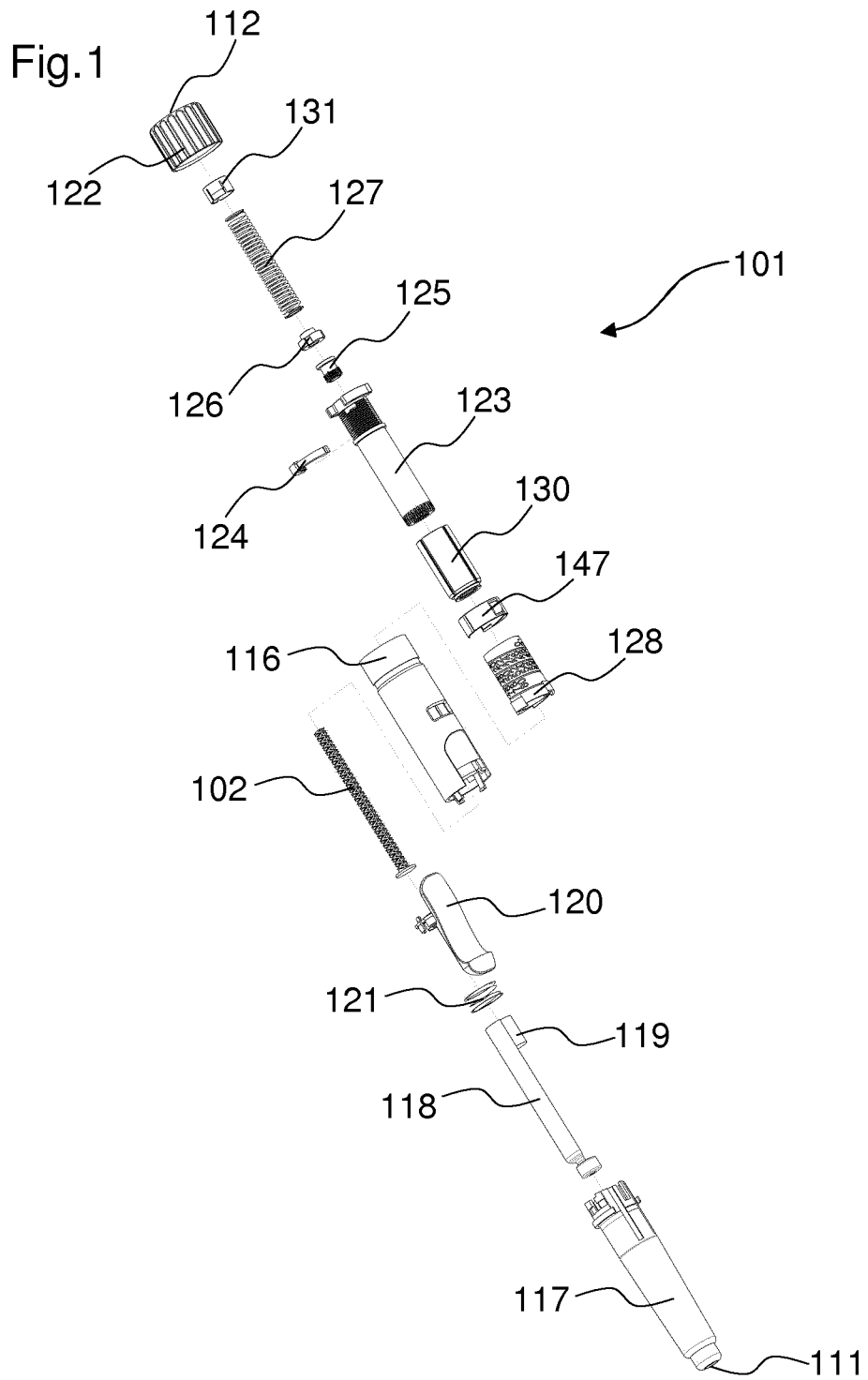
FIG. 1 shows an exploded view of a drug delivery device.

FIG. 1 shows an exploded view of a drug delivery device 101 and an assembly path for the components of the drug delivery device 101. In particular, the drug delivery device 101 is an injection device. The drug delivery device 101 is a variable dose device such that a user can select the size of a dose. The drug delivery device 101 is configured for multiple dose applications. The device can be delivered to a user in a fully assembled condition ready for use. The device has a low part count and is particularly attractive for cost sensitive device applications.

A cartridge 118 is housed within a cartridge holder 117. The cartridge holder 117 is rigidly constrained to a housing 116. An actuator 120 is rotationally constrained to the cartridge holder 117. Between the actuator 120 and the cartridge holder 117, a reset member 121 is arranged. The reset member 121 may be, for example, a spring. An axial force of the reset member 121 is transmitted to and counteracted by the cartridge holder 117. A piston rod 102 is configured to abut a piston 119 which is arranged in the cartridge 118. The piston rod 102 is configured to move the piston 119 in a direction towards a distal end 111 of the device, in order to deliver a medication from the cartridge 118. The piston rod 102 will be described later in more detail.

The drug delivery device 101 furthermore comprises an indicator 128, which is configured to indicate the amount of a set dose of a medication. The indicator 128 may be a number sleeve. The indicator 128 is coupled to a rotation member 123 by means of a coupling member 130. The rotation member 123 may be a sleeve. A window member 147 is placed over the indicator 128. The window member 147 comprises a transparent material. A last dose stop member 124 is engaged with the rotation member 123 by means of a thread. The last dose stop member 124 may be for example a lock nut. The last dose stop member 124 is configured to prevent the setting of a dose which is larger than the remaining amount of medication in the cartridge 118. A locking member 125 and a piston rod nut 126, which will be later described in more detail, are configured to engage with the piston rod 102. The piston rod nut 126 is configured as a drive control member. In particular, the piston rod nut 126 acts on the piston rod 102 for delivering a dose of medication. A spring member 127 is arranged between the piston rod nut 126 and a cap 131. The spring member 127 may be, for example, a coil spring. At a proximal end 112 of the device 101, a dose setting member 122 is arranged.

Figure 2:
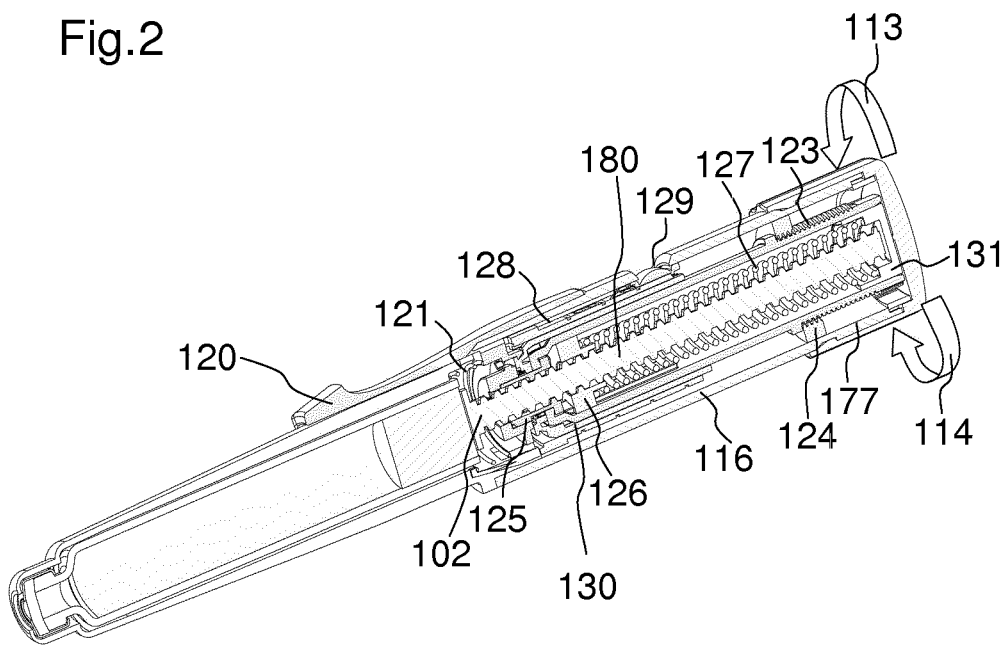
FIG. 2 shows a sectional view of the drug delivery device of FIG. 1 in an assembled state.

FIG. 2 shows a sectional view of the drug delivery device 101 in an assembled state. In particular, FIG. 2 shows a drive assembly 180. The dose setting member 122 can be rotated in a dose setting direction 113 in order to set a dose of medication. The dose setting direction 113 may be, for example, a clockwise direction. The force required to set and dispense a dose is consistent and independent of a force required to move the piston 119 within the cartridge 118. The dose setting member 122 can be rotated in a dose cancelling direction 114, in order to cancel a set dose of medication. The dose cancelling direction 114 may be, for example, a counter clockwise direction. The drug delivery device 101 permits a cancelling of a dose without any dose of medication being dispensed. When the dose setting member 122 is rotated in a dose setting or dose cancelling direction 113, 114, the rotation member 123 is also rotated due to an engagement of the dose setting member 122 and the rotation member 123, which will be later described in more detail. In particular, when the dose setting member 122 is rotated, the rotation member 123 is rotated with respect to the housing 116. The rotation member 123 is axially fixed with respect to the housing 116. When the rotation member 123 is rotated during the setting of a dose, the piston rod nut 126 is also rotated. Thereby, the piston rod nut 126 rotates about the piston rod 102 and moves towards a proximal end of the device 112. When the piston rod nut 126 moves towards a proximal end of the device 112, the spring member 127 is compressed between the cap 131 and the piston rod nut 126. In particular, the spring member 127 is compressed to store energy which is charged as a user selects the dose required. This energy is stored until the device is actuated in order to dispense a dose. At this point, the energy stored in the spring member 127 is used to deliver the medication from the cartridge 118 to a user.

The coupling member 130 is arranged concentrically around the rotation member 123. During dose setting, the coupling member 130 is engaged with the rotation member 123. Furthermore, the coupling member 130 is engaged with an indicator 128. The indicator 128 is arranged concentrically around the coupling member 130. In particular, the coupling member 130 is rotationally fixed with respect to the rotation member 123 and with respect to the indicator 128 during the setting of a dose. During the dispense of a dose, the coupling member 130 is engaged with the locking member 125 and the indicator 128. The coupling member 130 is configured to cause a rotation of the indicator 128 during the setting and dispense of a dose. The coupling member 130 and the indicator 128 will be later described in more detail.

Figure 3:
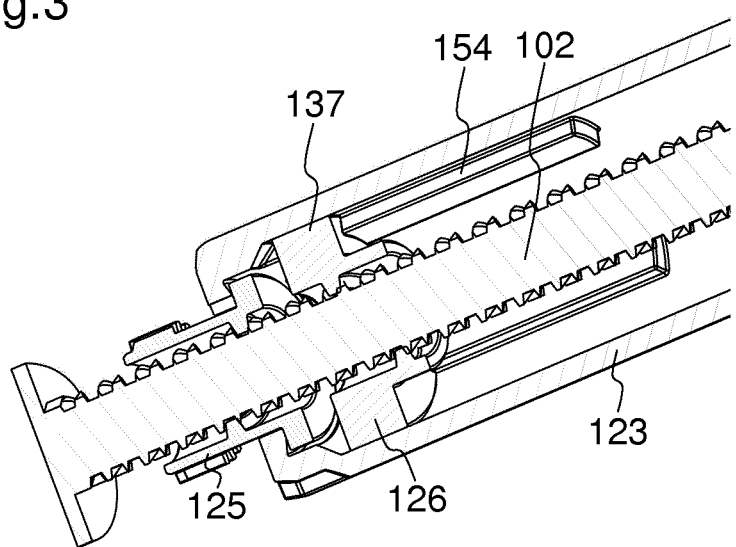
FIG. 3 shows a detailed view of the rotation member, the piston rod, the piston rod nut and the locking member.

FIG. 3 shows a more detailed view of the rotation member 123, the piston rod 102, the piston rod nut 126 and the locking member 125.

The piston rod nut 126 is in a threaded engagement with the piston rod 102. Furthermore, the piston rod nut 126 is rotationally fixed with respect to the rotation member 123. This is achieved by means of splines 137 of the piston rod nut 126, which engage in axial grooves 154 of the rotation member 123. In an alternative embodiment, the rotation member 123 and the piston rod nut 126 may be coupled by means of splines in the rotation member 123 and grooves in the piston rod nut 126. The piston rod nut 126 is axially moveable with respect to the rotation member 123 along the axial grooves 154 of the rotation member 123. The piston rod 102 is axially and rotationally fixed with respect to the housing 116 of the drug delivery device 101 during the setting and cancelling of a dose. This will be described more detailed in FIGS. 7 and 8.

During the setting or cancelling of a dose, the piston rod nut 126 rotates together with the rotation member 123 with respect to the housing 116 of the drug delivery device 101, since the piston rod nut 126 is rotationally fixed with respect to the rotation member 123. Thereby, the piston rod nut 126 rotates with respect to the piston rod 102. Due to the threaded engagement of the piston rod nut 126 and the piston rod 102, the piston rod nut 126 is screwed along the piston rod 102. This results in the piston rod nut 126 moving axially relative to the rotation member 123 and the piston rod 102. In particular, the piston rod nut 126 is moved in a direction towards a proximal end 112 of the device during the setting of a dose, and in a direction towards a distal end of the device during the cancelling of a dose. Furthermore, a locking member 125 is engaged with the piston rod 102. In particular, the locking member 125 is in threaded engagement with the piston rod 102. The thread of the locking member 125 has an opposing helix direction to the piston rod nut 126. During the setting of a dose, the locking member 125 is rotationally fixed with respect to the housing. Thereby, a movement of the piston rod 102 is inhibited during the setting of a dose. During a dispense of a dose, the locking member 125 is enabled to rotate with respect to the housing. In particular, the locking member 125 overhauls the piston rod 102. The torque which is needed to cause the locking member 125 to overhaul the piston rod 102 is provided by the spring member 127.

Figure 4:
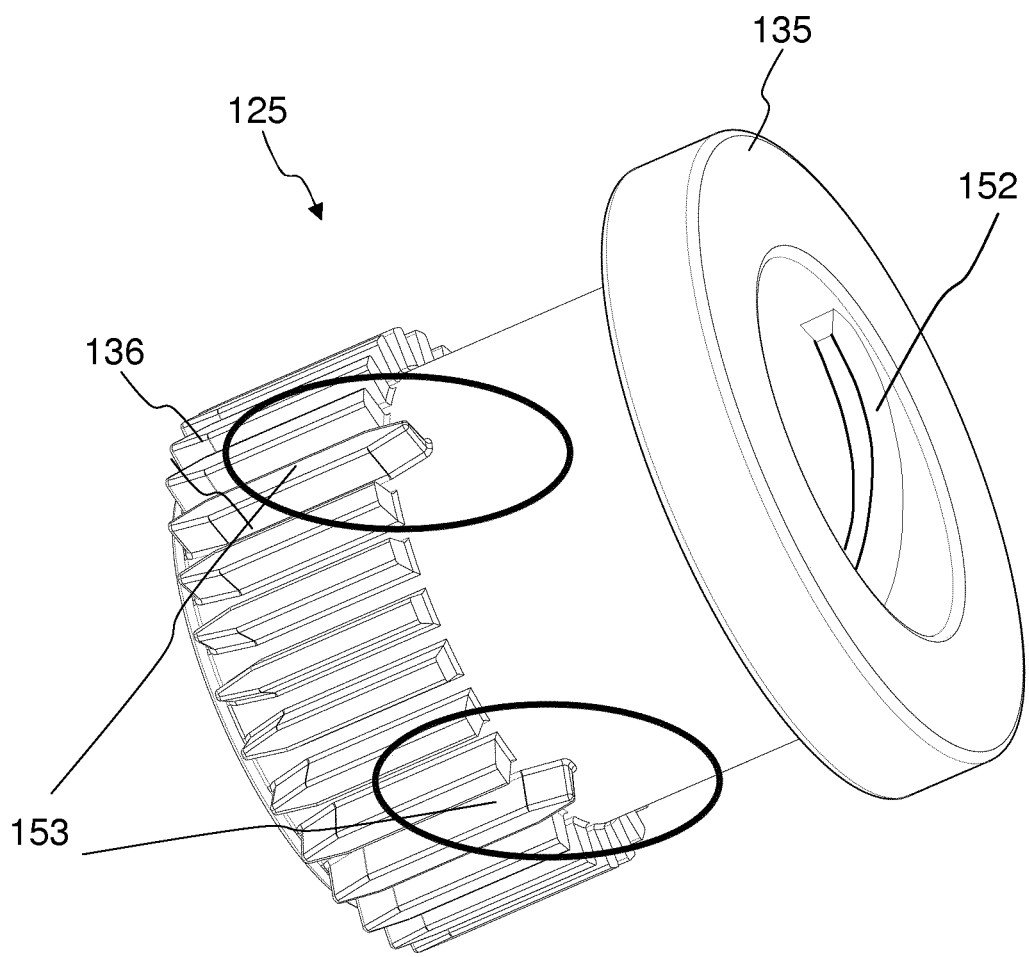
FIG. 4 shows a detailed view of the locking member.

FIG. 4 shows a more detailed view of the locking member 125. The locking member 125 is configured as a lock nut. The locking member 125 is in a threaded engagement with the piston rod by means of a thread 152. Furthermore, the locking member 125 comprises a plurality of splines 136. The splines 136 are arranged circumferentially around an outer circumference of the locking member 125. The splines 136 are configured to engage with the actuator 120 during the setting of a dose and with the coupling member 130 during the dispense of a dose. The locking member 125 may further comprise extended splines 153. The extended splines 153 may be arranged equally distributed between the splines 136. The ends of the extended splines 153 extend beyond the ends of the splines 136. The ends of the extended splines 153 may be chamfered. By means of the extended splines 153, misalignment tolerances may be diminished. Furthermore, due to the extended splines 153, molding of the locking member 125 may be permitted. The locking member 125 further comprises a flange 135. By means of the flange 135, the locking member 125 is axially fixed with respect to the housing 116 of the drug delivery device. In particular, the flange 135 abuts an internal surface of a distal end of the rotation member 123. During the setting of a dose, the locking member 125 is rotationally fixed with respect to the housing 116 due to an engagement with the actuator 120, which will be later described in more detail, for example with reference to FIG. 7.

Figure 5:
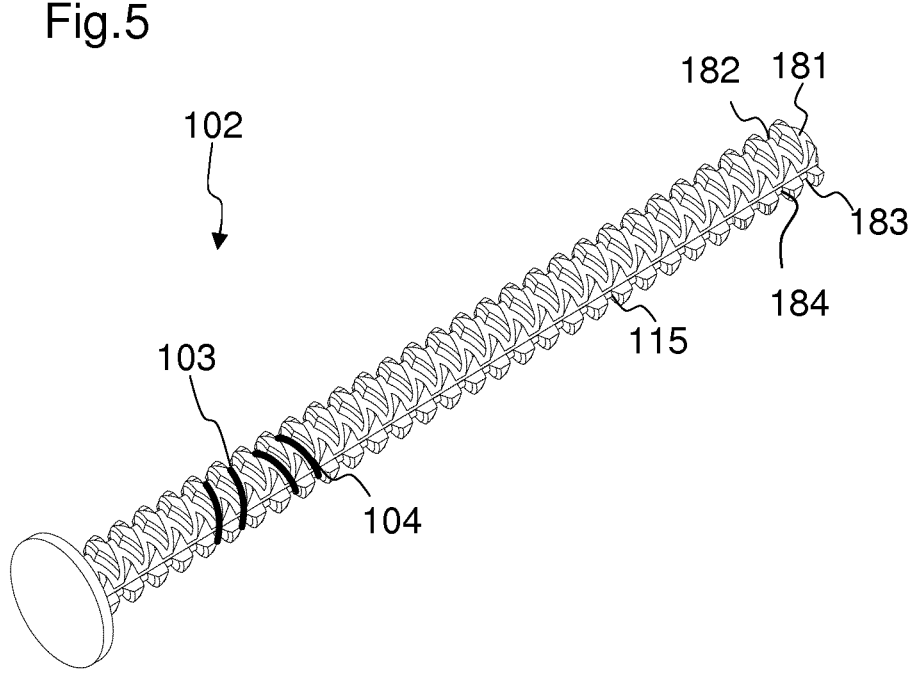
FIG. 5 shows a schematic view of the piston rod.

FIG. 5 shows a schematic view of the piston rod 102. The piston rod 102 is a lead-screw. The piston rod 102 comprises a first thread 103 and a second thread 104. The first and the second thread 103, 104 extend over the whole length of the piston rod 102. The first thread 103 and the second thread 104 are counter-handed. The pitch 105 of the first thread 103 is equal to the pitch 106 of the second thread 104. In an alternative embodiment, the pitch 105 of the first thread 103 may differ from the pitch 106 of the second thread. Since the first thread 103 and the second thread 104 are counter-handed, they intersect each other. The first thread 103 and the second thread 104 are twin start threads. The first thread 103 comprises two thread starts 181, 182. The second thread 104 comprises two thread starts 183, 184. The piston rod 102 comprises at least one axial spline 115. For example, the piston rod 102 may comprise two axial splines 115. The splines 115 run along the entire length of the piston rod 102. In FIG. 5, only one spline 115 is visible. The second spline is arranged opposite to the first spline 115. In particular, the splines 115 are arranged rotationally symmetric. The splines 115 are configured to engage with engagement features 133 of the actuator 120. Alternatively, the piston rod 102, in particular the splines 115, could engage directly with the housing 116. The locking member 125 is engaged with the first thread 103 of the piston rod 102. The pitch 105 of the first thread 103 engaging the locking member 125 is critical to ensure that an axial force applied to the piston rod 102 generates sufficient torque in the locking member 125 to overcome the thrust bearing friction at an interface between the locking member 125 and the rotation member 123. The piston rod nut 126 is engaged with the second thread 104 of the piston rod 102. The first thread 103 is a right handed thread. The second thread 104 is a left handed thread.

Figure 6:
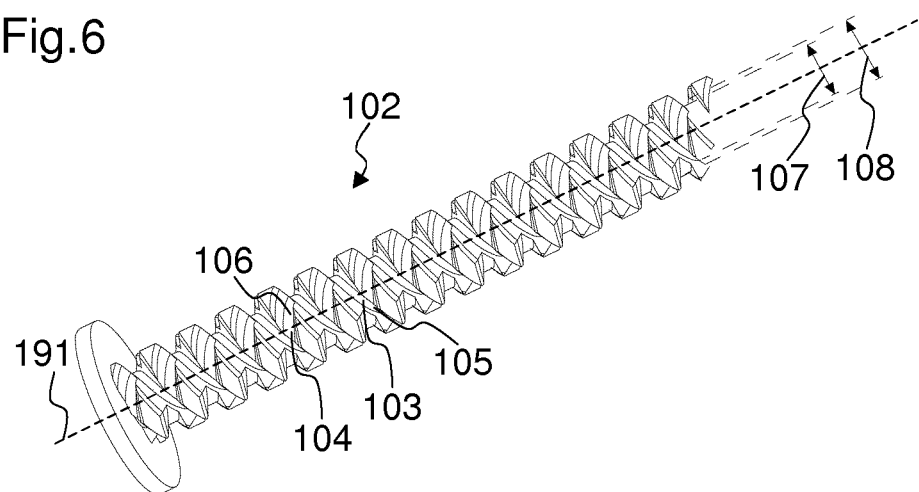
FIG. 6 shows a further embodiment of the piston rod.

FIG. 6 shows a preferred embodiment of the piston rod 102. The piston rod 102 shown in FIG. 6 is similar to the piston rod 102 shown in FIG. 5, except that a first inner diameter 107 of the first thread 103 is smaller than a second inner diameter 108 of the second thread 104. The first inner diameter 107 is the minor diameter of the first thread 103. The second inner diameter 108 is the minor diameter of the second thread. In particular, the first inner diameter 107 is two times the distance from a main axis 191 of the piston rod 102 to a surface of the pitch 105 of the first thread 103. In particular, the second inner diameter 108 is two times the distance from a main axis 191 of the piston rod 102 to a surface of the pitch 105 of the second thread 104. In particular, the first thread 103 is cut deeper than the second thread 104. One advantage of a piston rod 102 having a first inner diameter 107 of a first thread 103 which is smaller than a second diameter 108 of a second thread 104 is that the contact diameter between the first thread 103 and a member being engaged with the first thread 103, in particular the locking member 125, may be small. The smaller the contact diameter is, for a given thread pitch, the greater is a lead angle.

Increasing the lead angle reduces the frictional forces occurring at the thread interface. Therefore the smaller the contact diameter between the piston rod 102 and an overhauling element is, the smaller are the frictional losses. Therefore the overhauling force which has to be provided by the spring member 127 may be kept small compared to an assembly with a piston rod 102 with a larger inner diameter. In particular, when the locking member 125 overhauls the piston rod 102 during a dispense of a dose, a friction force between the locking member 125 and the piston rod 102 has to be overcome. The smaller the contact surface, respectively the contact diameter, between the piston rod 102 and an overhauling element, the smaller this friction force.

Due to the second inner diameter 108 being larger than the first inner diameter 107, the piston rod 102 still has a sufficient mechanical stability.

The piston rod 102 further comprises axial splines, which are not shown in this figure for clarity reasons. The splines are configured as shown in FIG. 5.

Figure 7:
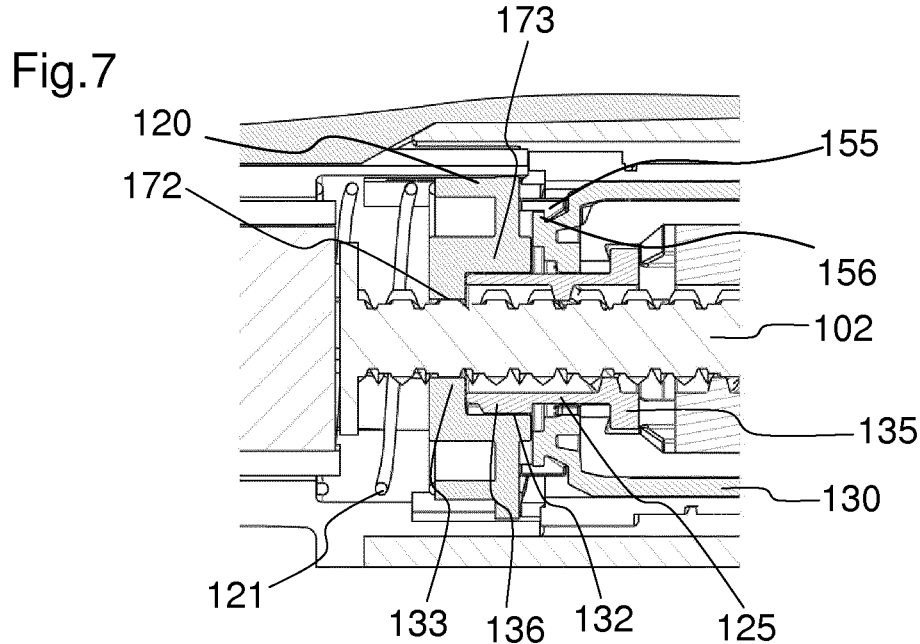
FIG. 7 shows the engagement of the actuator with the piston rod, the locking member and the coupling member during the setting of a dose.

FIG. 7 shows the engagement of the actuator 120 with the piston rod 102, the locking member 125 and the coupling member 130 during the setting of a dose or in a non-operating state, when the device is not in use. The actuator 120 is rotationally fixed with respect to the housing 116. The actuator 120 comprises an opening 172, through which the piston rod 102 extends. The actuator 120 is engaged with the locking member 125 by means of a first engagement feature 132 of the actuator 120. The first engagement feature 132 of the actuator 120 may comprise for example splines or teeth, which are arranged at a recess 173 of the actuator 120. The first engagement feature 132 of the actuator 120 engages with the splines 136 of the locking member 125. When the first engagement feature 132 of the actuator 120 is engaged with the splines 136 of the locking member 125, a rotational movement of the locking member 125 with respect to the actuator 120 is inhibited. Since the actuator 120 is rotationally fixed with respect to the housing 116 of the drug delivery device, the locking member 125 is also rotationally fixed with respect to the housing 116, when the first engagement feature 132 of the actuator 120 is engaged with the splines 136 of the locking member 125. Furthermore, the actuator 120 comprises second engagement features 133, which are engaged with the axial splines 115 of the piston rod 102. The second engagement features 133 are arranged at the opening 172 of the actuator 120. The second engagement features 133 of the actuator 120 may be configured as splines or protrusions. Thereby, the piston rod 102 is permanently rotationally fixed with respect to the housing 116 of the drug delivery device. Furthermore, the actuator 120 is engaged with the coupling member 130. In particular, the actuator 120 comprises a snap feature 155 which engages with an engagement feature 156 of the coupling member 130. The snap feature 155 of the actuator 120 may engage the engagement feature 156 of the coupling member 130 during an assembly of the device. Due to this engagement, the coupling member 130 is permanently axially fixed with respect to the actuator 120.

Figure 8:
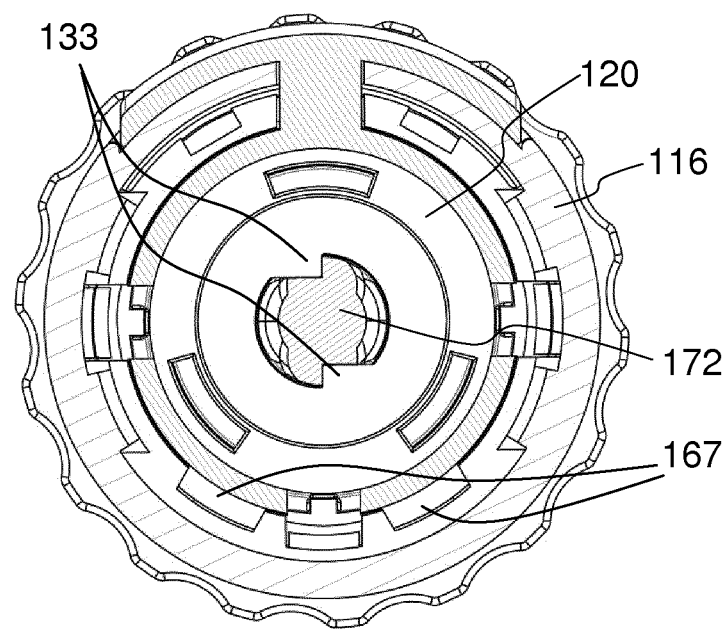
FIG. 8 shows the assembly of FIG. 7 in a sectional view.

FIG. 8 shows the actuator 120 of FIG. 7 in a cross-sectional view. In this embodiment, the second engagement features 133 of the actuator 120, which are configured to engage with the axial splines 115 of the piston rod 102, are shown. Furthermore, the actuator 120 comprises protrusions 167 which are engaged with grooves in the cartridge holder 117. Thereby, the actuator 120 is rotationally fixed with respect to the cartridge holder 117 and thereby rotationally fixed with respect to the housing 116, since the cartridge holder 117 is rigidly constrained to the housing 116. However, a limited axial travel of the actuator 120 is allowed.

Figure 9A:
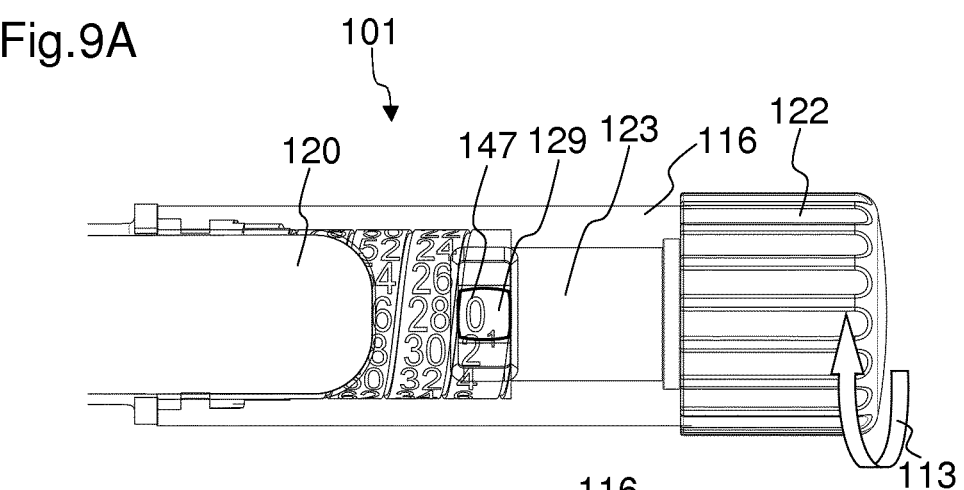
FIGS. 9A and 9B show a proximal part of the drug delivery device in an assembled state, with no dose set.
Figure 9B:
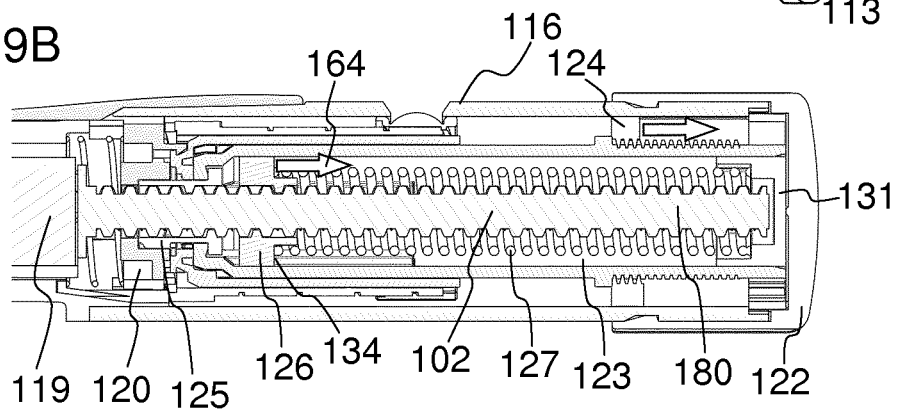

FIGS. 9A and 9B show a drive assembly 180 of the drug delivery device 101 in an assembled state. FIG. 9B shows the drive assembly 180 of the device 101 in a sectional view. In order to set a dose, the dose setting member 122 is rotated in a dose setting direction 113. When the dose setting member 122 is rotated, the rotation member 123 is also rotated. This is because the rotation member 123 is coupled with the dose setting member 122. The coupling of the rotation member 123 and the dose setting member 122 will be later described more detailed with reference to FIG. 20 and FIG. 21A to 21C. Since the piston rod nut 126 is rotationally fixed with respect to the rotation member 123, the piston rod nut 126 rotates with the rotation member 123. Thereby, the piston rod nut 126 is rotated about the piston rod 102 and moves axially along the piston rod 102 towards a proximal end of the device 112. When the piston rod nut 126 is moved towards the proximal end of the device, it compresses the spring member 127. Even when no dose is set, the spring member 127 is lightly compressed, since a minimum force greater than 0 N is required at the piston 119 for all dose sizes. When the dose setting member 122 is rotated in a dose cancelling direction, the piston rod nut 126 is moved towards the distal end of the device and the compression of the spring member 127 is released. The spring member 127 is arranged between the cap 131 and a proximal face 134 of the piston rod nut 126. Arrow 164 indicates the movement of the piston rod nut 126 during the setting of a dose. Arrow 165 indicates the movement of the last dose stop member 124 during the setting of a dose. The last dose stop member 124 and its functionality will be described more detailed with reference to FIGS. 18A to 18C.

Figure 10:
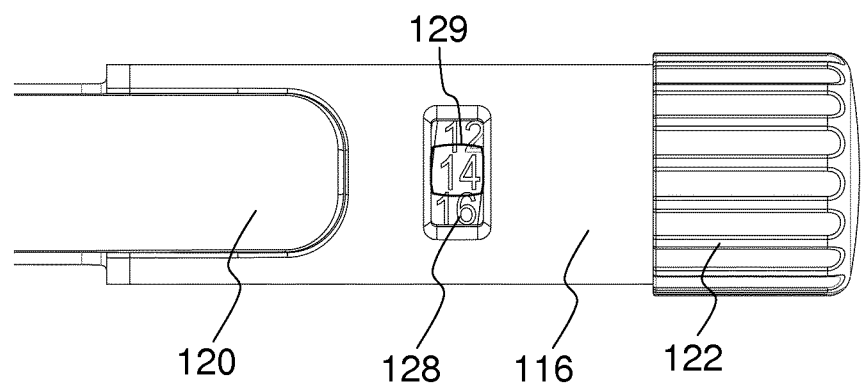
FIG. 10 shows the proximal part of a drug delivery device with an amount of a set dose being displayed in an indication window.

When the rotation member 123 is rotated during a setting or a cancelling of a dose, the coupling member 130 and the indicator 128 are also rotated. This is due to an engagement of the coupling member 130 with the rotation member 123, and an engagement of the indicator 128 with the coupling member, which is shown more detailed in FIG. 13. In particular, a rotation of the coupling member 130 results in a rotation and axial translation of the indicator 128. When the indicator 128 is rotated, the numbers shown in an indication window 129 indicate the dose which has been set. A single number on either side of the indication window 129 is also visible to aid in determining the required rotation of the dose setting member 122, as shown in FIG. 10. FIG. 10 shows the proximal part of a drug delivery device 101 with an amount of a set dose being displayed in the indication window 129.

In particular, the coupling member 130 rotates the indicator 128 during both set and dispense of a dose to ensure that the correct dose is displayed through the indication window 129. The indication window 129 is a cut-out in the housing of the drug delivery device. Between the indicator 128 and the indication window 129 a window member 147 is arranged. The window member 147 may prevent an intrusion of dust or dirt into the housing of the drug delivery device. A dose can be selected between zero and a predefined maximum in one unit increments. Any dose can be selected within this range. One unit is for example 0.01 ml.

Figure 11A:
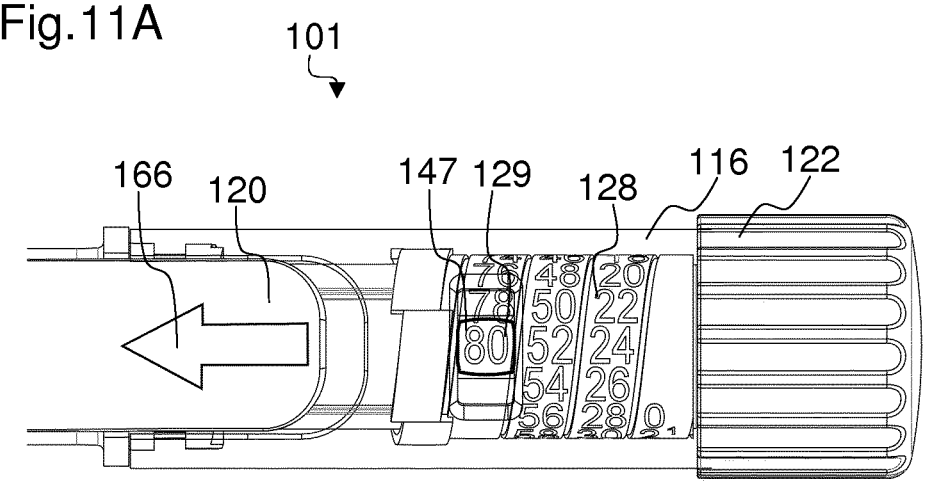
FIGS. 11A and 11B show the drug delivery device of FIGS. 9A and 9B in a state where a maximum dose has been set.
Figure 11B:
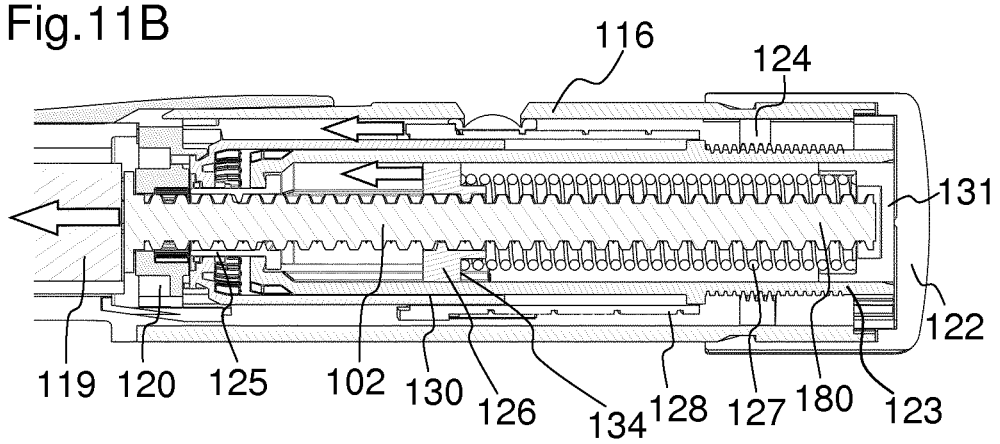

FIGS. 11A and 11B show the drug delivery device in a state where a dose has been set. In particular, a maximum dose has been set. The maximum is for example 80 units. FIG. 11B shows the device 101 in a sectional view. The amount of the set dose is indicated in the indication window 129. The amount of the set dose is indicated by the indicator 128. The indicator 128 is in its most proximal position. The spring member 127 is compressed by the piston rod nut 126. The last dose stop member 124 has translated axially in a proximal direction, compared to the position of the last dose stop member 124 shown in FIG. 9B. When the actuator 120 is actuated by a user, as indicated by an arrow 166 in FIG. 11A, in particular moved in the distal direction, the set dose of medication is delivered from the drug delivery device. When the actuator 120 is actuated, the locking member 125 is disengaged from the actuator 120. This mechanism will be later described in more detail with reference to FIGS. 23A to 23D. When the locking member 125 is disengaged from the actuator 120, the locking member 125 is enabled to rotate with respect to the housing 116. When the locking member 125 is enabled to rotate, the piston rod 102 is enabled to axially move with respect to the housing 116. During dispense, the locking member 125 is driven rotationally in the opposing direction to the direction of the rotation member 123 when setting a dose and, therefore, turns the indicator 128 backwards to reduce the value of the dose displayed.

The piston rod 102 moves in a direction towards a distal end 111 of the drug delivery device when a dose has been set and the actuator 120 is actuated. In particular, the spring member 127 exerts a force on the proximal face 134 of the piston rod nut 126. This force moves the piston rod 102 towards a distal end of the device. In particular, the piston rod 102 moves axially, but does not rotate with respect to the housing 116. When the piston rod 102 is moved in a direction towards a distal end of the device, the locking member 125 overhauls the piston rod 102. During the dispensing of a medication, the indicator 128 is moved back to its initial position.

Figure 12A:
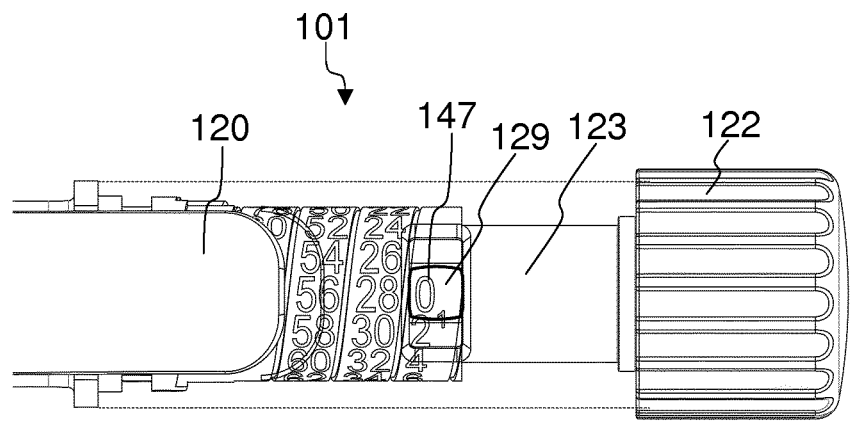
FIGS. 12A and 12B show the drug delivery device of FIGS. 9A, 9B, 11A and 11B in a condition when a dose of medication has been delivered from the device.
Figure 12B:
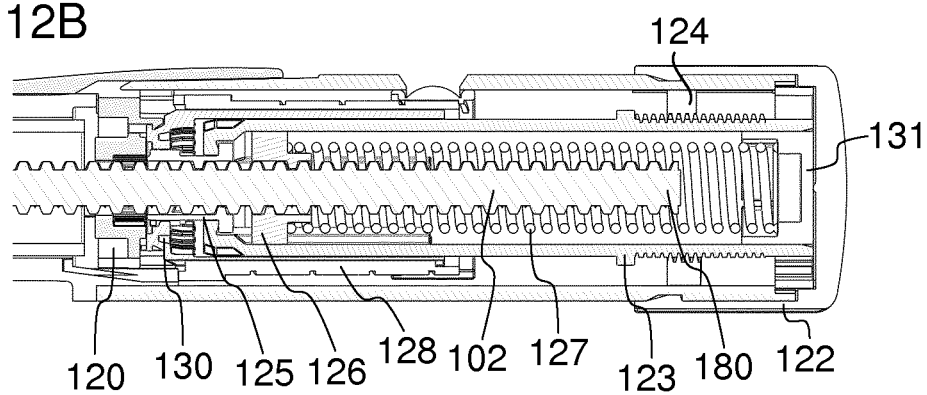

FIGS. 12A and 12B show the drug delivery device 101 in a condition when a dose of medication has been delivered from the device. All components besides the piston rod 102, the last dose stop member 124, the dose setting member 122, the rotation member 123, the locking member 125 and the piston rod nut 126 are in their initial position. In particular, the indicator 128 is in its initial position, such that the number "0" is shown in the indication window 129.

Figure 13:
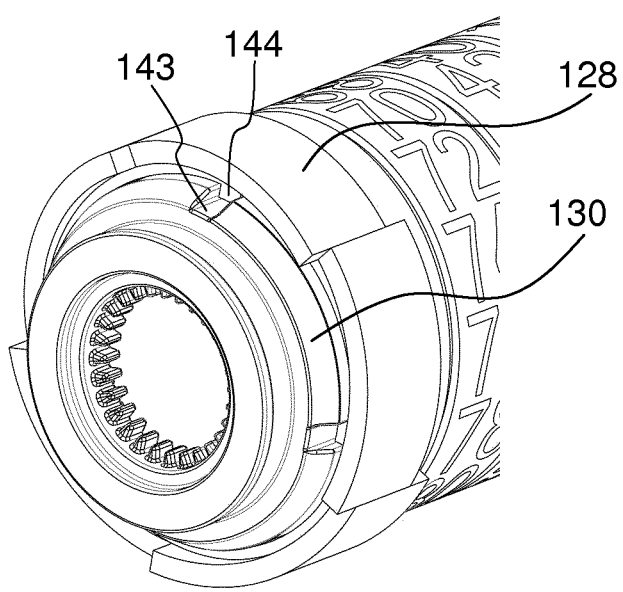
FIG. 13 shows the coupling member engaged with an indicator in a detailed view.

FIG. 13 shows the coupling member 130 engaged with the indicator 128 in a detailed view. In particular, the indicator 128 is rotationally constrained to the coupling member 130. This is achieved by engagement means 143 of the coupling member 130 being engaged with engagement means 144 of the indicator 128. For example, the engagement means 144 of the indicator 128 may be splines which engage with corresponding grooves in the coupling member 130. The indicator 128 and the coupling member 130 remain in engagement throughout the range of axial travel of the indicator 128.

Figure 14:
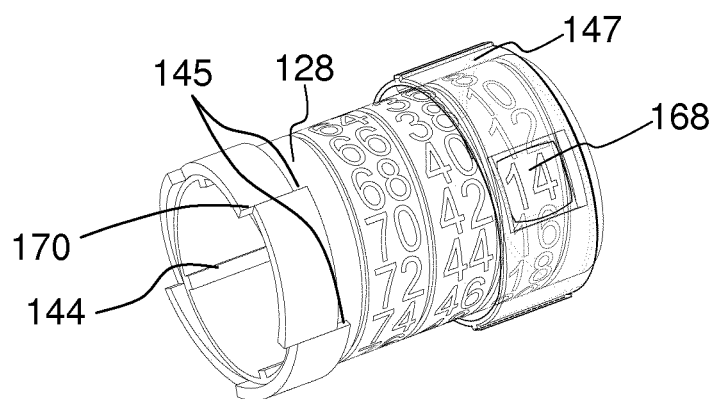
FIG. 14 shows a schematic view of the indicator and a window member.
Figure 16:
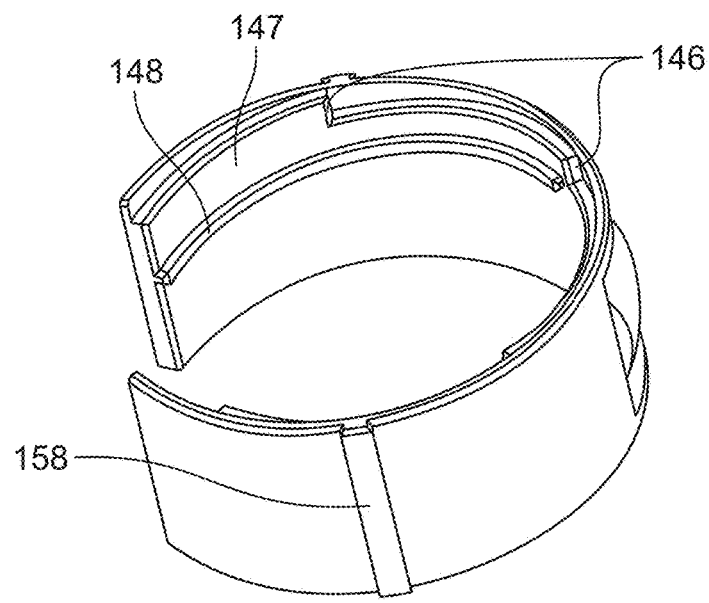
FIG. 16 shows a section of the window member.

FIG. 14 shows a schematic view of the indicator 128 and the window member 147, which is arranged concentrically around the indicator 128. The indicator 128 is printed with a helical path of numbers, the pitch of the helix matching the pitch of a thread connecting the indicator 128 and the window member 147. The thread 148 connecting the indicator 128 and the window member 147 is shown in FIG. 16. The number of the indicator 128 that is visible through the window member 147 corresponds to the set dose. The window member 147 comprises a magnifying element to make the numbers on the indicator 128 more distinct for a user. The indicator 128 comprises at least one maximum dose abutment 145. The window member 147 comprises at least one maximum dose abutment 146. The maximum dose abutment 146 inhibits the setting of a dose beyond a specified amount. The indicator 128 further comprises at least one stop feature 170. The stop feature 170 is configured to abut a stop feature 171 of the cartridge holder 117 when a set dose has been completely dispensed. In an alternative embodiment, the stop feature 171 may be located at the housing 116. In particular, the stop feature 170 acts as an end of dispense stop. Furthermore, the stop feature 170 acts as a dial down stop. This means that during the cancelling of a dose, the dose may not be dialled down farther than to zero units.

Figure 15A:
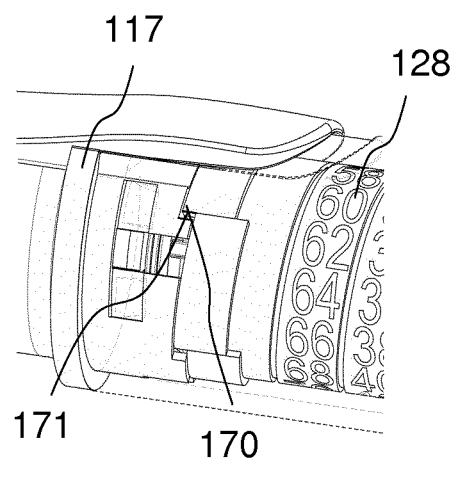
FIGS. 15A and 15B show a section of a cartridge holder and the indicator.
Figure 15B:
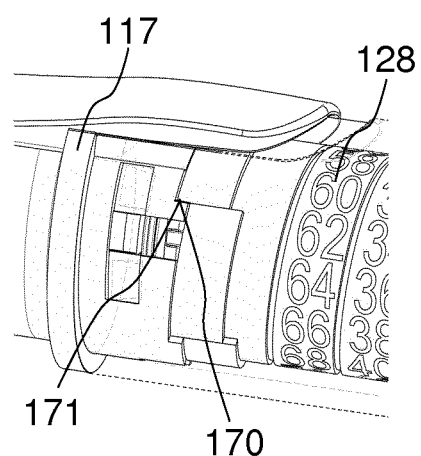

A section of the cartridge holder 117 and the indicator 128 are shown in FIGS. 15A and 15B. In FIG. 15A, the stop feature 170 of the indicator 128 approaches the stop feature 171 of the cartridge holder 117 during a dispense of a dose. In FIG. 15B, the stop feature 170 of the indicator 128 abuts the stop feature 171 of the cartridge holder 117. When the stop feature 170 of the indicator 128 abuts the stop feature 171 of the cartridge holder 117 a further rotation of the indicator 128 is inhibited. Accordingly, the cartridge holder 117 provides a rotational stop for the indicator 128 at the end of dose condition. Furthermore, when a rotation of the indicator 128 is inhibited, a rotation of the coupling member 130 is also inhibited. When a rotation of the coupling member 130 is inhibited, a rotation of the locking member 125 is inhibited. Thereby, the dispense of a dose of medication is inhibited.

In FIG. 16, a section of the window member 147 is shown in more detail. The window member 147 is configured to be connected to the indicator 128 via a thread 148. Furthermore, the window member 147 comprises engagement means 158. The engagement means 158 of the window member 147 are configured to engage with the housing 116. Thereby, a rotation of the window member 147 relative to the housing 116 is inhibited. In particular, the window member 147 is rigidly constrained to the housing 116. For example, the engagement means 158 of the window member 128 may be splines. Alternatively, the engagement means 158 may be grooves.

Figures 17A, 17B, 17C:
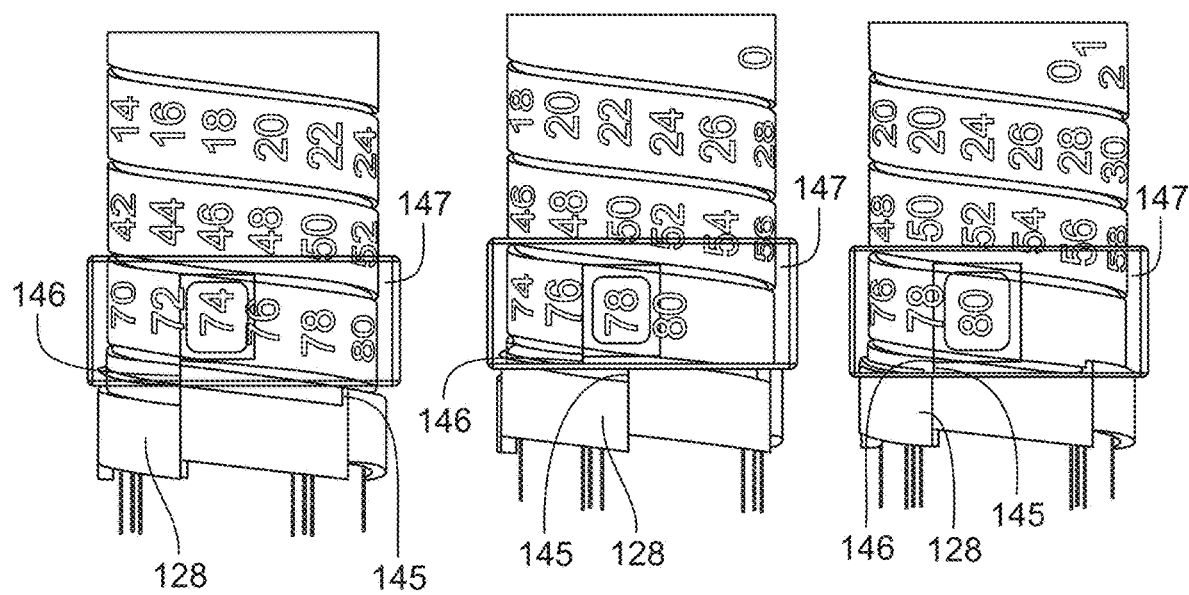
FIGS. 17A to 17C show the window member and the indicator in three different states during an operation of the drug delivery device.

FIGS. 17A to 17C show the window member 147 and the indicator 128 in three different states during the setting of a dose. The indicator 128 is threaded to the window member 147 such that rotation of the indicator 128 by the coupling member 130 results in a rotation and axial translation of the indicator 128 with respect to the window member 147. During the setting of a dose, the maximum dose abutment 146 of the indicator 128 approaches the maximum dose abutment 146 of the window member 147, as shown in FIGS. 17A and 17B. When a maximum dose has been set, the maximum dose abutment 145 of the indicator 128 abuts the maximum dose abutment 146 of the window member 147, as shown in FIG. 17C. Thereby, a further rotation of the indicator 128 is inhibited. Thereby, the setting of a dose beyond a maximum dose is inhibited. The maximum dose is visible through the window member 147.

Figures 18A, 18B, 18C:
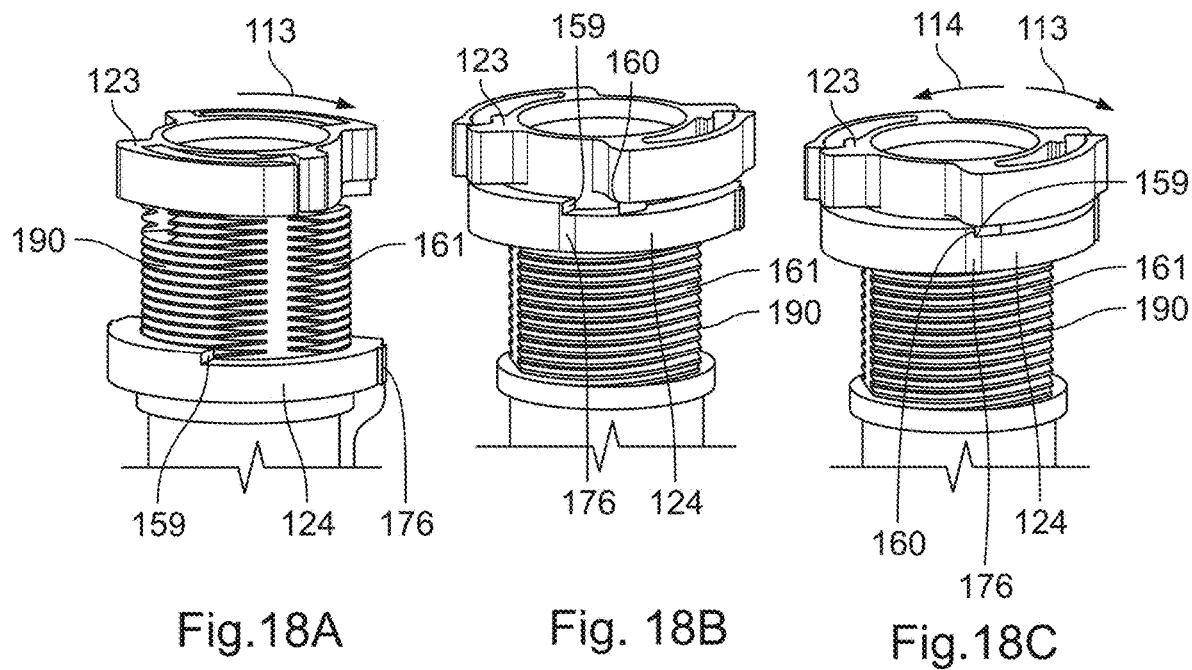
FIGS. 18A to 18C show the engagement of the last dose stop member with the rotation member in three different states.

FIGS. 18A to 18C show the position of the last dose stop member 124 relative to the rotation member 123 in three different states of the device. The rotation member 123 acts as a last dose stop drive member 190. The number of permissible rotations of the rotation member 123 relative to the last dose stop member 124 is determined by the capacity of the cartridge 118. In particular, a movement of the rotation member 123 results in a movement of the last dose stop member 124. The last dose stop member 124 is rotationally fixed but axially movable with respect to the housing 116. This is achieved by means of at least one protrusion 176 of the last dose stop member 124, which is configured to engage with the housing 116, for example with at least one axial groove 177 (see FIG. 2) of the housing 116. The last dose stop member 124 is engaged with the rotation member 123 by means of a thread 161. The last dose stop member 124 comprises a last dose stop member abutment 159. FIG. 18A shows the last dose stop member 124 in a position before any dose has been set. When the rotation member 123 is rotated in a dose setting direction 113 the last dose stop member 124 moves along the rotation member 123 towards a proximal end of the device. When only a small amount of medication is left in a cartridge, a last dose stop face 160 of the rotation member 123 approaches the last dose stop face 159 of the last dose stop member 124 as can be seen in FIG. 18B. When the last dose stop face 160 of the rotation member abuts the last dose stop face 159 of the last dose stop member 124, as shown in FIG. 18C, a further setting of a dose is inhibited. This is because further rotation of the rotation member 123 in a dose setting direction 113 is inhibited. Thereby, the setting of a dose which is larger than a dose of medication remaining in the cartridge is inhibited. Yet, the cancelling of a set dose of medication is still possible by rotating the rotation member 123 in a dose cancelling direction 114. When the rotation member 123 is rotated in the dose cancelling direction 114, the last dose stop member 124 is moved towards the distal end 111 of the device.

Figure 19:
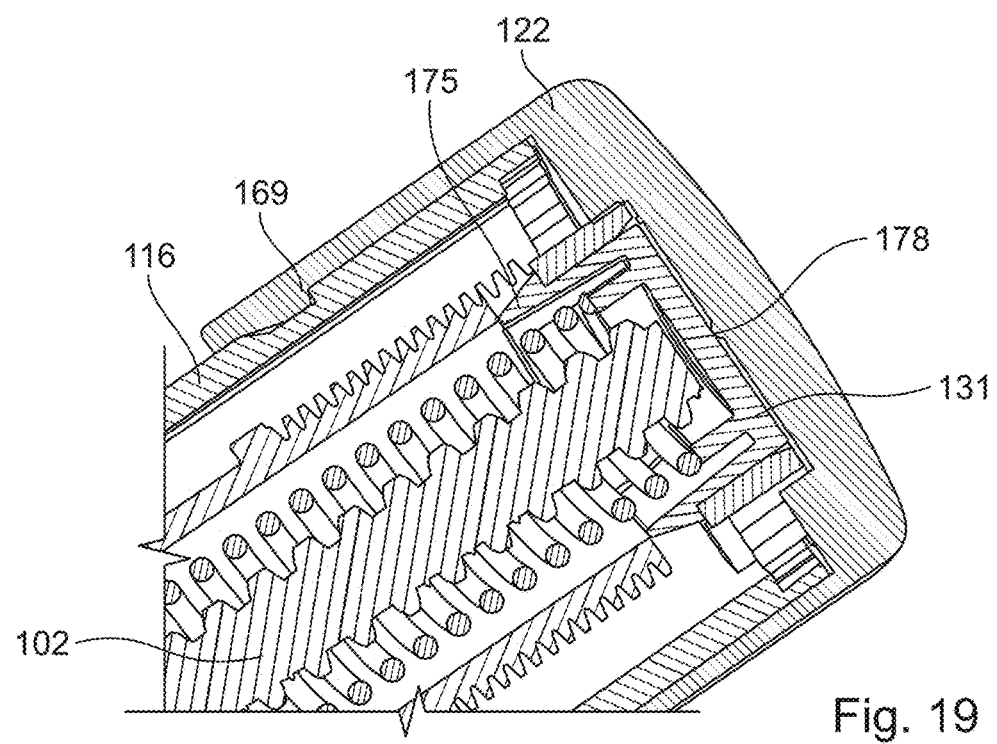
FIG. 19 shows a section through the proximal end of the drug delivery device.

FIG. 19 shows a section through the proximal end of the drug delivery device. This section shows an axial constraint between the housing 116 and the dose setting member 122 by means of a protrusion 169 in the housing 116. Furthermore, the arrangement of the cap 131 is shown. The cap 131 is constrained within the dose setting member 122. The cap 131 contacts a distal surface of the dose setting member 122 via a small diameter bearing 178. Through this interface, a force of the piston 119 acting on the piston rod 102 is transmitted to and counteracted by the housing 116. In particular, the small diameter bearing 178 provides a bearing for the rotation member 123. Furthermore, the spring member 127 contacts the cap 131. The cap 131 is axially fixed to the rotation member 123 via constraint features 175 which engage with the rotation member 123.

Figure 20:
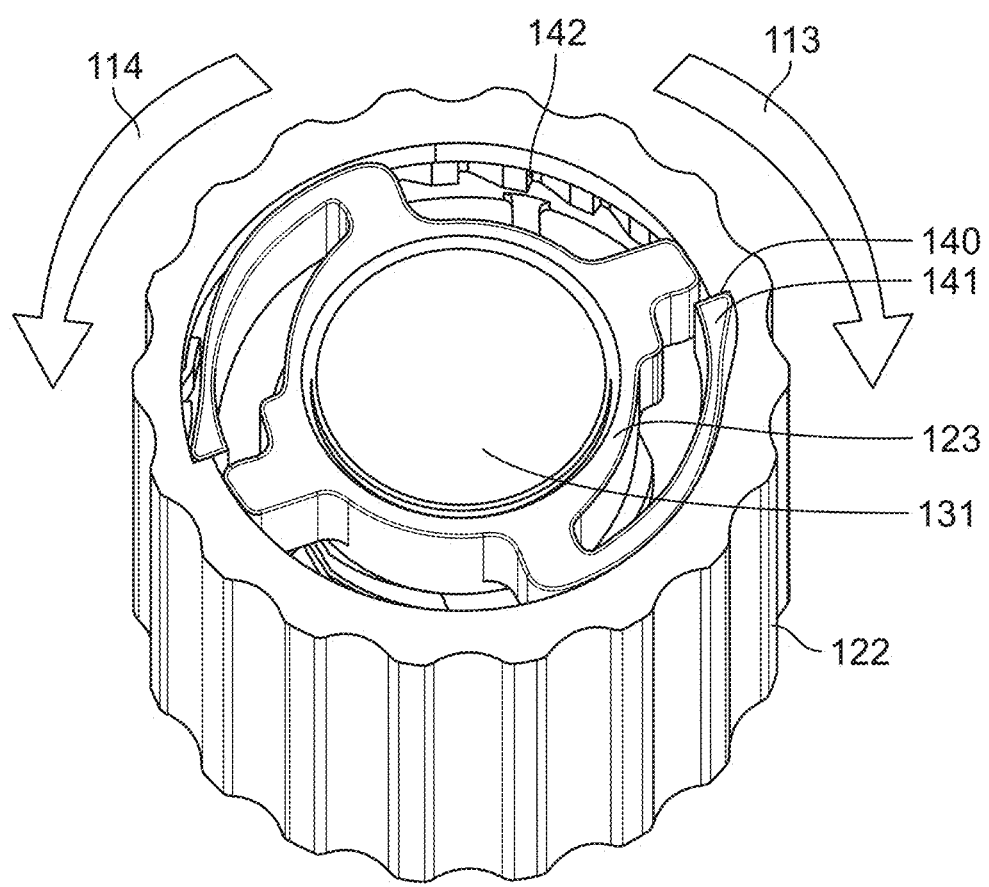
FIG. 20 shows the engagement of the rotation member with the dose setting member.

FIG. 20 shows the engagement of the rotation member 123 with the dose setting member 122. The rotation member 123 is mounted on the cap 131. The dose setting member 122 comprises at least one, for example two ratchet features 140. The ratchet features 140 are configured as indentations in the dose setting member 122. The rotation member 123 comprises at least one, for example two ratchet arms 141. The ratchet arms 141 of the rotation member 123 engage with the ratchet features 140 of the dose setting member 122. When the dose setting member 122 is not rotated, for example during the dispense of a dose, or when the dose setting member 122 is rotated in a dose setting direction, the ratchet arms 141 abut the ratchet features 140 of the dose setting member 122. When an axial spring force, provided by the spring member 127, acts on the piston rod nut 126, a torque is created by the piston rod nut 126 trying to overhaul the threaded interface with the piston rod 102. Due to the engagement of the piston rod nut 126 with the rotation member 123, a tangential force is transmitted to the rotation member 123. Thereby, the rotation member 123 may be caused to rotate, for example during the cancelling of a dose, when the ratchet arms 141 of the rotation member 123 do not abut the ratchet features 140 of the dose setting member 122. During the cancelling of a dose, there may be a gap between the ratchet arms 141 and the ratchet features 140 for a short duration. In particular, the ratchet arms 141 may disengage from the ratchet features 140 for a short duration during the cancelling of a dose. The ratchet arms 141 of the rotation member 123 are furthermore in engagement with a housing ratchet feature 142 of a housing of the drug delivery device. The housing ratchet feature 142 may be for example a plurality of teeth or indentations located at an inner circumference of the housing 116.

The ratchet interface between the dose setting member 122 and the housing 116 ensures that the torque generated by the spring member 127 acting on the piston rod nut 126 does not return the device to a zero-unit position when a user releases the dose setting member 122 after a dose has been set. The zero-unit position is a position where no unit of a dose is set.

Figure 21A:
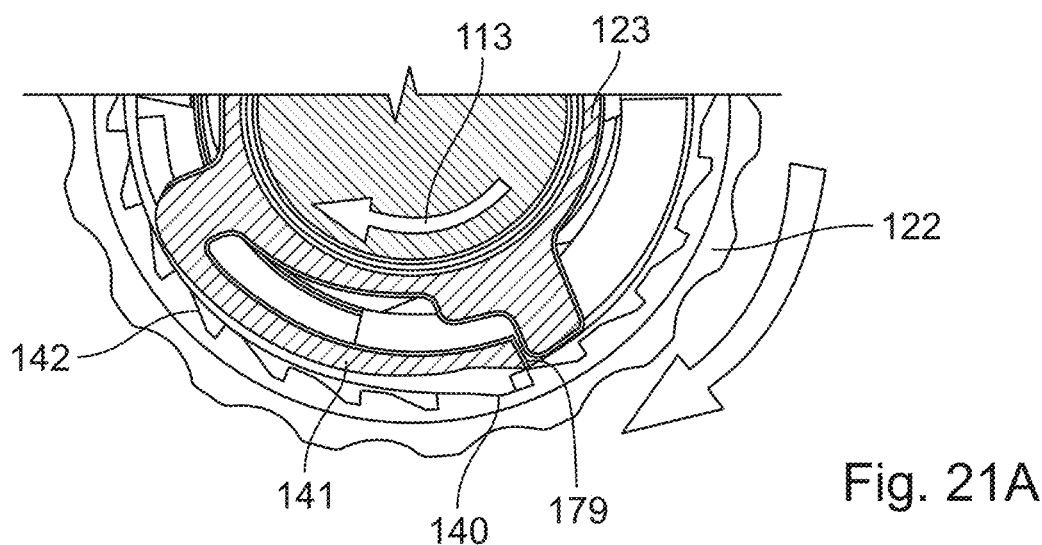
FIG. 21A to 21C show the dose setting member and the rotation member according to FIG. 20 in three different states.
Figure 21B:
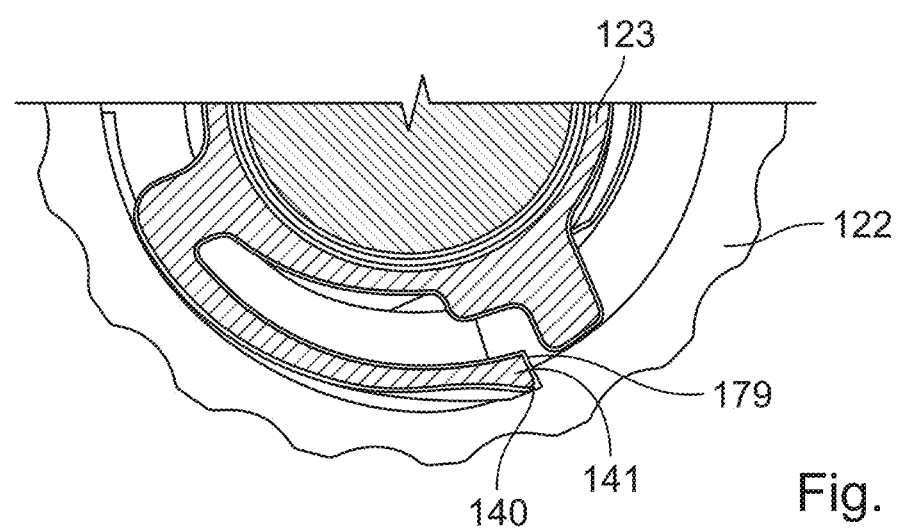
Figure 21C:
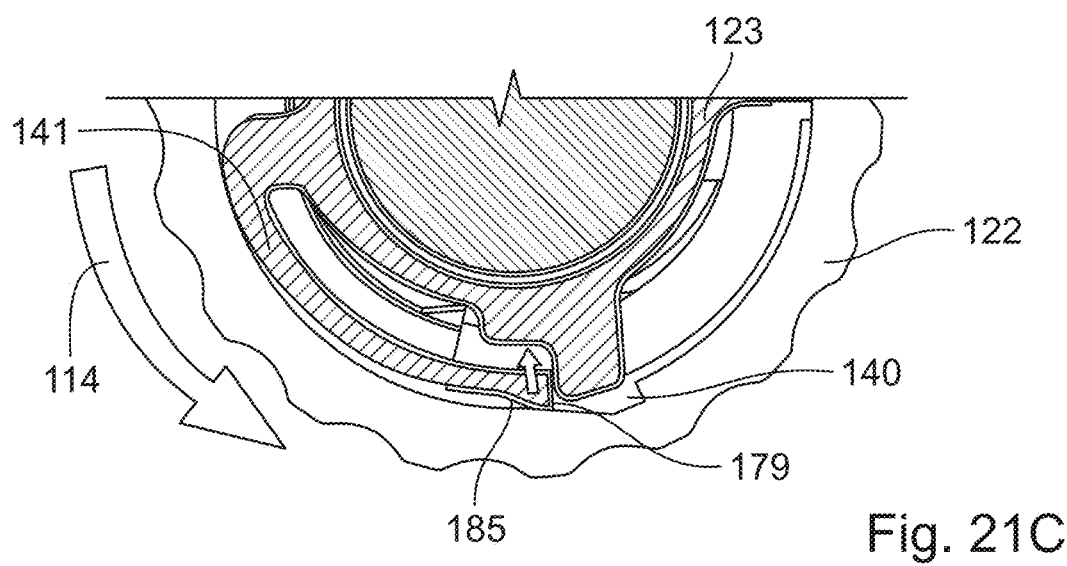

FIG. 21A to 21C show the dose setting member 122 and the rotation member 123 according to FIG. 20, in particular the ratchet feature 140 of the dose setting member 122 and the ratchet arms 141 of the rotation member 123 in three different states.

FIG. 21A shows the engagement of the dose setting member 122 and the rotation member 123 in a state during the setting of a dose. When the dose setting member 122 is rotated in a dose setting direction 113, the rotation member 123 is rotated with it due to the engagement of the ratchet arms 141 with the ratchet feature 140 of the dose setting member 122. In particular, the dose setting member 122 acts on a radial face 179 of the ratchet arm 141 and rotates the rotation member 123 directly, forcing it to engage with a subsequent indentation or tooth of the housing ratchet feature 142. The ratchet feature 140 is configured as an indentation in the dose setting member 122. An inner circumference of the dose setting member 122 slightly extends over the housing ratchet feature 142 of the housing in a direction towards a longitudinal axis of the drug delivery device. In particular, the ratchet feature 140 of the dose setting member 122 is enlarged with respect to the housing ratchet feature 142. Therefore, the ratchet arm 141 of the rotation member 123 can disengage from the housing ratchet feature 142 when the dose setting member 122 is rotated in a dose setting direction 113, but can not disengage from the ratchet feature 140 of the dose setting member 122. A ramp angle of the ratchet feature 140 is reduced in order to ensure that the ratchet arm 141 fully reengages with the housing ratchet feature 142 before it abuts the ratchet feature 140. This is to prevent a user from experiencing shock load through the dose setting member 122. When the ratchet arm 141 reengages with the housing ratchet feature 142, an audible feedback may be given to a user. Furthermore, the housing ratchet feature 142 may inhibit an unintended rotation of the rotation member 123 in a dose cancelling direction.

FIG. 21B shows the rotation member 123 and the dose setting member 122 in a condition when the dose setting member 122 is not rotated. This state may temporarily also occur during a rotation of the dose setting member 122. In this state, the ratchet arms 141 of the rotation member is fully engaged with the ratchet feature 140 of the dose setting member and with the housing ratchet feature 142.

FIG. 21C shows the rotation member 123 and the dose setting member 122 during the cancelling of a dose. When the dose setting member is rotated in a dose cancelling direction 114, the ratchet arm 141 is temporally disengaged from the ratchet feature 140 of the dose setting member. Furthermore, the ratchet arm 141 is disengaged from the housing ratchet feature 142. This is because the ratchet arm 141 is deflected in a radial inward direction by the dose setting member 122. This is achieved by the dose setting member 122 acting on a sloped face 185 of the ratchet arm 141. Due to the torque acting on the rotation member 123 by the spring member 127, the rotation member is rotated in a dose cancelling direction until the ratchet arms 141 reengage with the ratchet feature 140 of the dose setting member. The dose setting member 122 can now be turned in either direction to increase or decrease the set dose.

FIG. 22 shows an alternative embodiment of the dose setting member 122. In this embodiment, a ratchet arm spring force required is reduced. Thereby, a dialling torque is reduced. This embodiment comprises additional engagement features 162, which engage with an abutment of the rotation member 123. The additional engagement features 162 are configured as lugs. The dose setting member 122 comprises two lugs. The strength of the engagement between the dose setting member 122 and the rotation member 123 is increased, when the dose setting member 122 is rotated in a dose setting direction 113. Furthermore, this engagement drives the rotation member 123 in the dose cancelling direction 114. The engagement features 162 of the dose setting member 122 are configured to rotate the rotation member 123 in a dose setting direction 113. Thereby, the ratchet arms 141 of the rotation member 123 are unburdened during the setting of a dose. Thereby, the ratchet arms 141 may be prevented from being damaged. In particular, the ratchet arms 141 perform the single function of resisting the torque generated by the spring member 127 acting on the piston rod nut 126. In particular, they do not transfer the rotation of the dose setting member 122 in a rotation of the rotation member 123. The rotation of the rotation member 123 is only achieved by means of the engagement features 162. An additional benefit is removal of a sliding friction interface between the dose setting member 122 and the ratchet arm 141.

FIGS. 23A to 23D explain the operation of the mechanism when the actuator 120 is actuated and a dose is dispensed. The force required for actuating the actuator 120 and the distance which it has to move are small, providing a significant ergonomic advantage, particularly for such users with impaired dexterity.

Figure 23A:
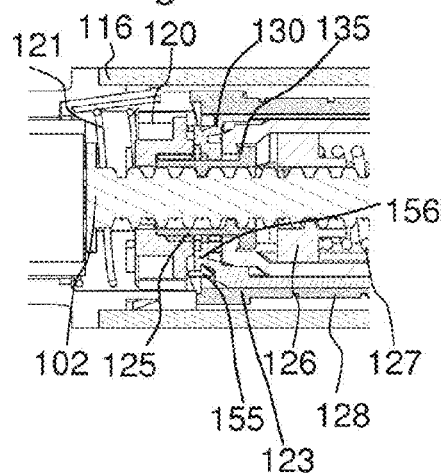
Figure 23B:
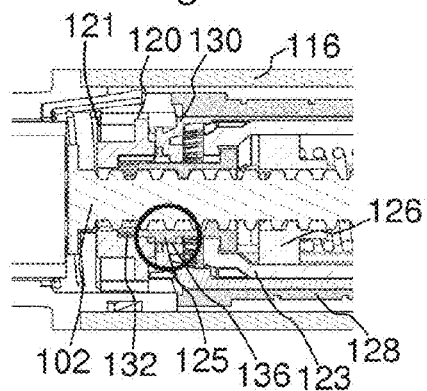
Figure 23C:
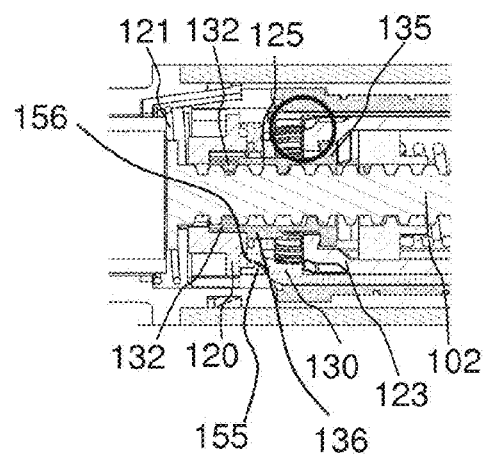
Figure 23D:
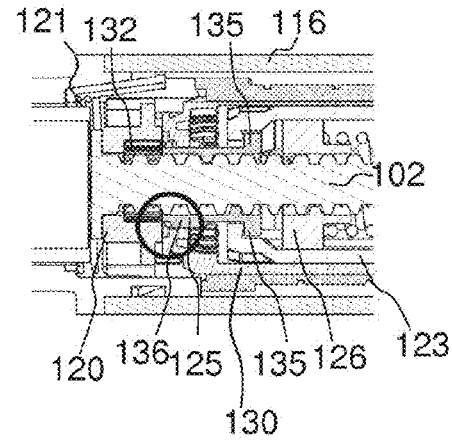

FIG. 23A shows the mechanism before the actuator 120 is actuated. The locking member 125 is engaged with the actuator 120 and thereby rotationally fixed with respect to the housing 116 of the drug delivery device. The coupling member 130 is rotationally fixed with respect to the rotation member 123 due to an engagement of the coupling member 130 with the rotation member 123 and, therefore, in a locking state. In particular, the coupling member 130 is in a locking state as long as the dose setting member 122 is not rotated by a user. Since the locking member 125 is in its locking state due to its engagement with the actuator 120, the piston rod 102 is axially and rotationally fixed with respect to the housing. In particular, the locking member 125 is non-rotatable with respect to the piston rod 102. When the actuator 120 is moved towards the distal end of the device, as shown in FIG. 23B, the coupling member 130 is moved with the actuator 120. This is due to the engagement of the snap feature 155 of the actuator with the engagement feature 156 of the coupling member 130. The locking member 125 remains in its axial position due to the flange 135 of the locking member abutting a surface of the rotation member 123.

When the actuator 120 is further moved towards a distal direction as shown in FIG. 21B the coupling member 130 is pulled into engagement with the splines 136 of the locking member 125. Thereby, the coupling member 130 is rotationally fixed with respect to the locking member 125. When the actuator 120 has reached the position shown in FIG. 23C, the coupling member 130 is completely disengaged from the rotation member 123. When the actuator 120 has reached the position shown in FIG. 23D, the engagement between the locking member 125 and the actuator 120 is released. In particular, the first engagement feature 132 of the actuator 120 is disengaged from the splines 136 of the locking member 125. When the locking member 125 is completely disengaged from the actuator 120 it is enabled to rotate with respect to the housing 116. Thereby, the piston rod 102 is enabled to axially move with respect to the housing 116. When the piston rod 102 is enabled to move, in particular when the locking member 125 is enabled to rotate, a force of the spring member 127 is released. In particular, the spring member 127 is enabled to relax. In particular, the piston rod 102 is moved in a distal direction by the force of the spring member 127. In particular, the spring member exerts a force on the piston rod nut 126, thereby moving the piston rod nut 126 and together with it the piston rod 102. Thereby, the locking member 125 overhauls the piston rod 102.

When the spring member 127 acts on the proximal surface of the piston rod nut 126, thereby moving the piston rod 102 in a distal direction, the flange 135 of the locking member 125 is pressed against the inner surface of the rotation member 123. Thereby, the rotation of the locking member 125 is impeded. When the torque which is needed to overhaul the piston rod 102 is less, the force of the spring member 127 acting on the piston rod nut 126 may be reduced, and the locking member 125 is pressed against the inner surface of the rotation member 123 with less force. Thereby, the frictional losses at the interface between the flange 135 of the locking member 125 and the inner surface of the rotation member 123 can be reduced. This can be achieved by using a piston rod 102 wherein the inner diameter 107 of the first thread 103 is smaller than the inner diameter 108 of the second thread 104. Such a piston rod 102 is shown in FIG. 6.

Since the coupling member 130 is in engagement with the splines 136 of the locking member 125, the coupling member 130 rotates together with the locking member 125. In particular, the coupling member rotates in a direction which is counter-wise to the rotation of the coupling member 130 during the setting of a dose. Thereby, the coupling member 130 rotates the indicator 128 back to its initial position.

The reset member 121 reacts on a proximal face of the cartridge holder 117. It provides a return force in the proximal direction to return the actuator 120 to its initial position when a user releases the actuator 120.

Figure 24:
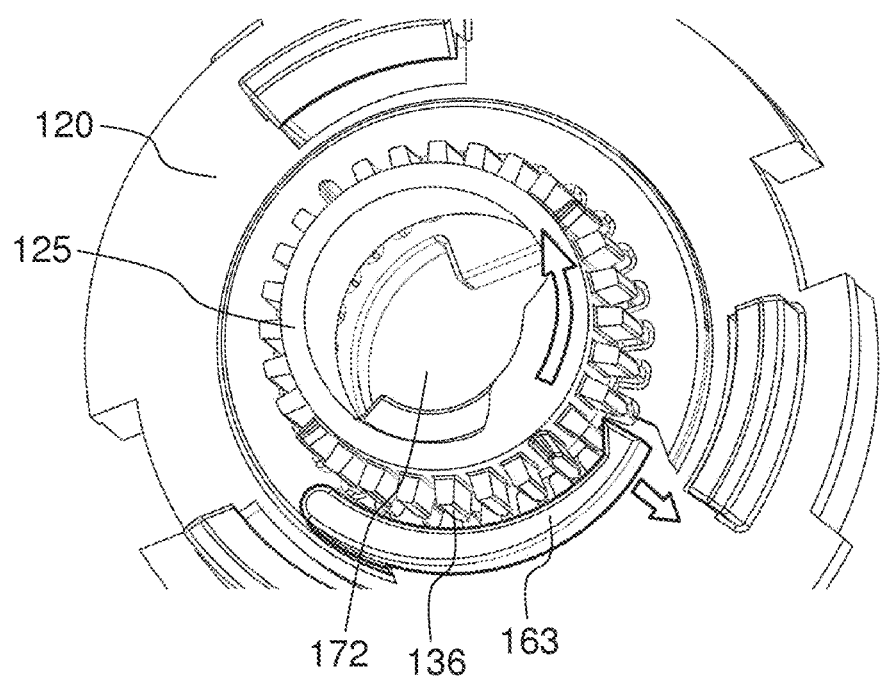
FIG. 24 shows the actuator and the locking member during the dispensing of a dose.

FIG. 24 shows the actuator 120 and the locking member 125 during the dispensing of a dose. In this state, the locking member 125 is enabled to rotate with respect to a housing of the drug delivery device, in particular with respect to the actuator 120. The actuator 120 comprises a feedback feature 163, which may be, for example, a flexible arm. The feedback feature 163 may be lightly engaged with the splines 36 of the locking member 125. When the locking member 125 rotates, in particular when the splines 136 pass the feedback feature 163, the feedback feature 163 is deflected in a radially outward direction, in particular in a direction away from a longitudinal axis of the drug delivery device. When one spline passes the feedback feature 163, an audible click is produced. In particular, a click is produced when the feedback feature 163 rapidly returns to its undeflected position. Each click corresponds to the dispense of a single unit. This is because the number of splines 136 on the locking member 125 is equal to the number of units dispensed during one rotation of the locking member 125.

Figure 25A:
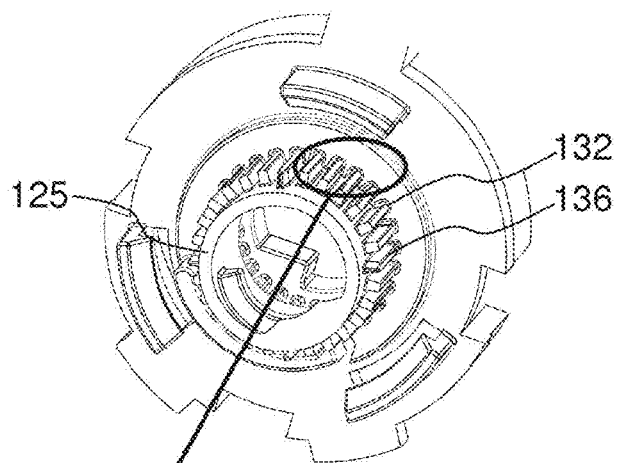
FIGS. 25A to 25C illustrate a reengagement of the actuator with the locking member after a dose has been dispensed.
Figure 25B:
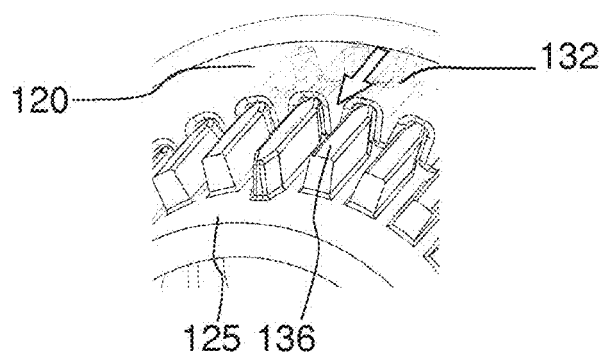
Figure 25C:
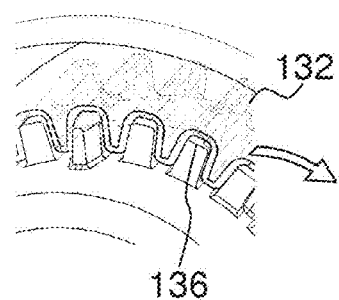

FIGS. 25A to 25C illustrate a reengagement of the actuator 120 with the locking member 125 after a dose has been dispensed and the actuator 120 has been released. When the actuator 120 is released, the first engagement feature 132 of the actuator 120 reengages with the splines 136 of the locking member 125. The engagement features 132 of the actuator 120 are angled such that during a reengagement the locking member 125 is rotated against the torque being produced by the spring member 127. Thereby, the locking member 125 is wound back a small distance. Thereby, the piston rod is retracted a small distance. This back-winding of the locking member 125 removes the effect of clearances within the mechanism, which are a result of manufacturing tolerances. These tolerances could otherwise lead to slight advancement of the piston rod and a dispense of a dose of medication. The back-winding of the locking member 125 retracts the piston rod 102 and ensures that the locking member 125 is acting as the dispense stop in place of the indicator 128.

The invention claimed is:

1. A piston rod for a drug delivery device, the piston rod comprising:
   a first thread with a first inner diameter; and
   a second thread with a second inner diameter,
   wherein the first inner diameter is smaller than the second inner diameter, and
   wherein the first thread comprises a first pitch and the second thread comprises a second pitch, the first pitch and the second pitch having a same magnitude,
   wherein the first thread extends in a first section of the piston rod and the second thread extends in a second section of the piston rod, the first thread extending along a portion of the piston rod along which the second thread extends,
   wherein the first and second sections overlap, and
   wherein the first thread and the second thread intersect each other.

2. The piston rod according to claim 1, wherein the first and the second threads are counter-handed.

3. The piston rod according to claim 1, wherein at least one of the first or second threads extends over a whole length of the piston rod.

4. The piston rod according to claim 1, wherein at least one of the first or second threads is a twin-start thread.

5. The piston rod according to claim 1, comprising at least one axial spline or at least one axial groove.

6. A drug delivery device comprising:
   a cartridge containing a medication; and
   a piston rod to dispense the medication during dose dispensing, the piston rod comprising
      a first thread with a first inner diameter; and
      a second thread with a second inner diameter,
      wherein the first inner diameter is smaller than the second inner diameter,
      wherein the first thread comprises a first pitch and the second thread comprises a second pitch, the first pitch and the second pitch having a same magnitude,
      wherein the first thread extends in a first section of the piston rod and the second thread extends in a second section of the piston rod, the first thread extending along a portion piston rod along which the second thread extends,
      wherein the first and second sections overlap, and
      wherein the first thread and the second thread intersect each other.

7. The drug delivery device according to claim 6, comprising a housing, wherein the piston rod is rotationally fixed to the housing.

8. The drug delivery device according to claim 7, comprising a locking member being engaged with the first thread of the piston rod, wherein a movement of the piston rod is inhibited when the locking member is in a locking state.

9. The drug delivery device according to claim 8, wherein the locking member is in the locking state during dose setting, and wherein the locking member is free to rotate during the dose dispensing.

10. The drug delivery device according to claim 8, wherein the locking member is configured to overhaul the piston rod during the dose dispensing.

11. The drug delivery device according to claim 8, comprising a piston rod nut engaged with the second thread of the piston rod and configured to rotate along the piston rod in a direction towards a proximal end of the drug delivery device to set a dose of the medication.

12. The drug delivery device according to claim 11, comprising a spring member configured to cause the piston rod to move toward a distal end of the drug delivery device by exerting a force on the piston rod nut.

13. The drug delivery device according to claim 8, comprising an actuator, wherein the locking member is released from its locking state when the actuator is activated.

14. The drug delivery device according to claim 13, wherein the actuator is in engagement with at least one axial spline or groove of the piston rod, thereby inhibiting rotation of the piston rod relative to the housing.

15. The drug delivery device according to claim 6, wherein the first and second threads are counter-handed.

16. The drug delivery device according to claim 6, wherein at least one of the first or second threads extends over a whole length of the piston rod.

17. The drug delivery device according to claim 6, wherein the medication comprises at least one pharmaceutically active compound.

18. The drug delivery device according to claim 6, wherein the portion of the piston rod along which the first and second threads extend is an axially oriented portion.

* * * * *

UNITED STATES PATENT AND TRADEMARK OFFICE
CERTIFICATE OF CORRECTION

PATENT NO. : 10,737,035 B2
APPLICATION NO. : 14/915952
DATED : August 11, 2020
INVENTOR(S) : Simon Lewis Bilton Page 1 of 1

It is certified that error appears in the above-identified patent and that said Letters Patent is hereby corrected as shown below:

In the Claims

In Column 22, Line 17, Claim 6, after "portion" insert -- of the --

Signed and Sealed this
Twentieth Day of October, 2020

Andrei Iancu
*Director of the United States Patent and Trademark Office*